United States Patent
Ashton et al.

(10) Patent No.: US 7,026,316 B2
(45) Date of Patent: Apr. 11, 2006

(54) DIPEPTIDYL PEPTIDASE INHIBITORS FOR THE TREATMENT OR PREVENTION OF DIABETES

(75) Inventors: Wallace T. Ashton, Edison, NJ (US); Charles G. Caldwell, Scotch Plains, NJ (US); Hyun O. Ok, Edison, NJ (US); Emma R. Parmee, Scotch Plains, NJ (US); Ann E. Weber, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 202 days.

(21) Appl. No.: 10/472,771

(22) PCT Filed: Mar. 22, 2002

(86) PCT No.: PCT/US02/08931

§ 371 (c)(1),
(2), (4) Date: Sep. 24, 2003

(65) Prior Publication Data

US 2004/0106656 A1    Jun. 3, 2004

Related U.S. Application Data

(60) Provisional application No. 60/278,931, filed on Mar. 27, 2001.

(51) Int. Cl.
| | | |
|---|---|---|
| A61K 31/426 | (2006.01) | |
| A61K 31/40 | (2006.01) | |
| C07D 207/00 | (2006.01) | |
| C07D 277/04 | (2006.01) | |
| C07D 417/04 | (2006.01) | |

(52) U.S. Cl. .................. 514/242; 514/326; 514/365; 514/397; 514/423; 546/209; 546/269.7; 546/270.4; 548/181; 548/200; 548/314.7; 548/540

(58) Field of Classification Search ............. 548/181, 548/200, 314.7, 540; 546/209, 269.7, 270.4; 514/326, 242, 365, 397, 423
See application file for complete search history.

(56) References Cited

U.S. PATENT DOCUMENTS 5,939,560 A    8/1999  Jenkins et al.
6,090,786 A    7/2000  Augustyns et al.
6,201,132 B1   3/2001  Jenkins et al.
2003/0004138 A1  1/2003  Wierzbicki et al.

FOREIGN PATENT DOCUMENTS

| WO | WO 97/40832    | 11/1997 |
| WO | WO 98/19998    | 5/1998  |
| WO | WO 02/14271    | 2/2002  |
| WO | WO 02/38541    | 5/2002  |
| WO | WO 03/002530 A2 | 1/2003 |
| WO | WO 03/002530 A3 | 1/2003 |
| WO | WO 03/002531 A2 | 1/2003 |
| WO | WO 03/002531 A3 | 1/2003 |
| WO | WO 03/024942   | 3/2003  |

OTHER PUBLICATIONS

Golub et al., Science, Vol. 286, Oct. 15, 1999, pp. 531-537.*
Ashworth, D. M., et al., "2-Cyanopyrrolidides As Potent, Stable Inhibitors Of Dipeptidyl Peptidase IV", Bioorganic & Medicinal Chemistry Letters, Vol. 6, No. 10, pp. 1163-1166 (1996).
Ashworth, D. M., et al., "4-Cyanothiazolidides As Very Potent, Stable Inhibitors of Dipeptidyl Peptidase IV", Biorganic & Medicinal Chemistry Letters, Vol. 6, No. 22, pp. 2745-2748 (1996).
Augustyns, K. J. L., et al., "Pyrrolidides: synthesis and structure-activity relationship as inhibitors of dipeptidyl peptidase IV", Eur J Med Chem, 32, pp. 301-309 (1997).

* cited by examiner

*Primary Examiner*—Laura L. Stockton
(74) *Attorney, Agent, or Firm*—Philippe L. Durette; Melvin Winokur

(57) ABSTRACT

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

23 Claims, No Drawings

DIPEPTIDYL PEPTIDASE INHIBITORS FOR THE TREATMENT OR PREVENTION OF DIABETES

CROSS REFERENCE TO RELATED APPLICATIONS

This application is the National Stage of International Application No. PCT/US02/08931, filed 22 Mar. 2002, which claims the benefit under 35 U.S.C. 119(e) of U.S. Provisional Application No. 60/278,931, filed 27 Mar. 2001.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance. Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the PPAR agonists, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6(10), 1163–1166 (1996); and Bioorg. Med. Chem. Lett., 6(22), 2745–2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues. DP-IV inhibitors may also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions.

SUMMARY OF THE INVENTION

The present invention is directed to compounds which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention is directed to compounds of formula I:

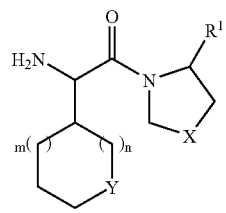

wherein:
X is selected from —S—, —S(O)—, —S(O)$_2$—, —CH$_2$—, —CHF—, and —CF$_2$—;
Y is selected from CH—(C$_{0-4}$alkyl-R$^2$) and N—R$^3$;
m is an integer selected from 0, 1 and 2, and n is an integer selected from 0, 1 and 2, with the proviso that the sum of m+n is 1 or 2;
R$^1$ is selected from hydrogen and —CN;
R$^2$ is selected from the group consisting of:
 (1) —NR$^4$—CO—NR$^5$R$^6$,
 (2) —NR$^4$—CO$_2$R$^6$,
 (3) —NR$^4$—COR$^6$,
 (4) —NR$^5$R$^6$,
 (5) —NH$_2$,
 (6) —NR$^4$—S(O)$_2$—R$^6$,
 (7) —S(O)$_2$—NR$^5$R$^6$,
 (8) —CO—NR$^5$R$^6$,
 (9) —O—CO—NR$^5$R$^6$,
 (10) —OH,
 (11) —O—R$^6$,
 (12) —R$^6$, and
 (13) hydrogen, with the proviso that R$^2$ is hydrogen only if X is —CHF— or —CF$_2$—;
R$^3$ is selected from the group consisting of:
 (1) —CO—NR$^5$R$^6$,
 (2) —CO$_2$R$^6$,
 (3) —COR$^6$,
 (4) —S(O)$_2$—R$^6$,
 (5) —R$^6$, and
 (6) hydrogen, with the proviso that R$^3$ is hydrogen only if X is —CHF— or —CF$_2$—;
R$^4$ and R$^5$ are independently selected from hydrogen and C$_{1-6}$alkyl;
R$^6$ is independently selected from:
 (1) C$_{1-10}$alkyl, which is unsubstituted or substituted, where the substituents are independently selected from:
  (a) hydroxy,
  (b) —O—C$_{1-6}$alkyl,
  (c) halogen,
  (d) phenyloxy, and
  (e) —CN;
 (2) phenyl, phenyloxy, C$_{1-6}$alkyl-phenyl, naphthyl, C$_{1-6}$alkyl-naphthyl, biphenyl, C$_{1-6}$alkyl-biphenyl, wherein the phenyl, naphthyl, or biphenyl, is unsubstituted or substituted, where the substituents are independently selected from:
  (a) halogen,
  (b) —OCF$_3$,
  (c) —CF$_3$,
  (d) —CHF$_2$,
  (e) —CH$_2$F,
  (f) C$_{1-10}$alkyl,
  (g) —O—C$_{1-6}$alkyl,
  (h) —O-phenyl, wherein the phenyl is unsubstituted or substituted, where the substituents are independently selected from:
   (i) halogen,
   (ii) —OCF$_3$,
   (iii) —CF$_3$,
   (iv) C$_{1-6}$alkyl, and
   (v) —O—C$_{1-6}$alkyl,
  (i) —CN,
  (j) hydroxy,
  (k) —NR$^8$R$^9$, wherein R$^8$ and R$^9$ are independently selected from hydrogen and C$_{1-6}$alkyl, or R$^8$ and R$^9$ are joined together with the nitrogen to form a 5–6 membered ring,
  (l) —NR$^4$—CO—NR$^8$R$^9$,
  (m) —NR$^4$—S(O)$_2$—C$_{1-6}$alkyl,
  (n) —CO—NR$^8$R$^9$,
  (o) —CO$_2$—C$_{1-6}$alkyl,
  (p) —O—CO—NR$^8$R$^9$, and
  (q) heterocycle, wherein the heterocycle is unsubstituted or substituted, where the substituents are independently selected from:
   (i) halogen,
   (ii) oxo,
   (iii) C$_{1-10}$alkyl-(C$_{3-6}$cycloalkyl),
   (iv) C$_{1-10}$alkyl, which is unsubstituted or substituted with up to 5 halogen,
   (v) —O—C$_{1-6}$alkyl, which is unsubstituted or substituted with up to 5 halogen,
   (vi) C$_{0-6}$alkyl-phenyl, wherein the phenyl is unsubstituted or substituted, where the substituents are independently selected from:
    (I) halogen,
    (II) —OCF$_3$,
    (III) —CF$_3$,
    (IV) C$_{1-6}$alkyl, and
    (V) —O—C$_{1-6}$alkyl,
   (vii) pyridyl, and
   (viii) —CO—C$_{1-6}$alkyl;
 (3) heterocycle, and C$_{1-6}$alkyl-heterocycle, wherein the heterocycle is unsubstituted or substituted, where the substituents are independently selected from:
  (a) halogen,
  (b) oxo,
  (c) C$_{1-10}$alkyl-(C$_{3-6}$cycloalkyl),
  (d) C$_{1-10}$alkyl, which is unsubstituted or substituted with up to 5 halogen,
  (e) —O—C$_{1-6}$alkyl, which is unsubstituted or substituted with up to 5 halogen,
  (f) C$_{0-6}$alkyl-phenyl, wherein the phenyl is unsubstituted or substituted, where the substituents are independently selected from:
   (i) halogen,
   (ii) —OCF$_3$,
   (iii) —CF$_3$, (iv) C$_{1-6}$alkyl, and
(v) —O—C$_{1-6}$alkyl,
(g) pyridyl, and
(h) —CO—C$_{1-6}$alkyl;

and pharmaceutically acceptable salts thereof and individual diastereomers thereof.

Preferred compounds of the present invention include those of formula Ia:

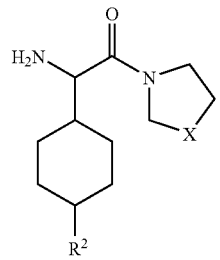

Ia wherein X and R$^2$ are defined herein;

and pharmaceutically acceptable salts and individual diastereomers thereof.

Preferred compounds of the present invention include those of formula Ib:

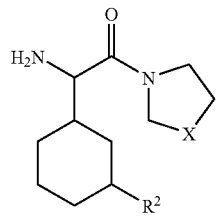

Ib wherein X and R$^2$ are defined herein;

and pharmaceutically acceptable salts and individual diastereomers thereof.

Preferred compounds of the present invention include those of formula Ic:

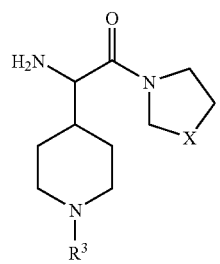

Ic wherein X and R$^3$ are defined herein;

and pharmaceutically acceptable salts thereof and individual diastereomers thereof.

Preferred compounds of the present invention include those of formula Id:

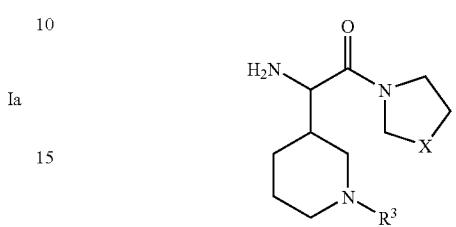

Id wherein X and R$^3$ are defined herein;

and pharmaceutically acceptable salts thereof and individual diastereomers thereof.

Preferred compounds of the present invention include those of formula Ie:

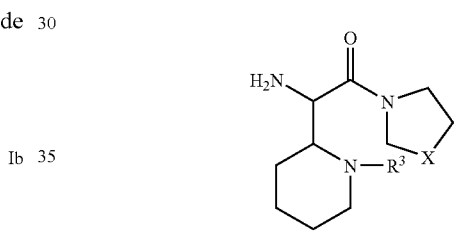

Ie wherein X and R$^3$ are defined herein;

and pharmaceutically acceptable salts thereof and individual diastereomers thereof.

Preferred compounds of the present invention include those of formula If:

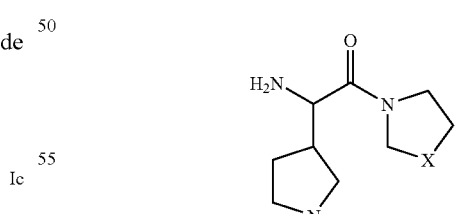

If wherein X and R$^3$ are defined herein;

and pharmaceutically acceptable salts and individual diastereomers thereof.

Another group of compounds of the present invention include those of formula Ig:

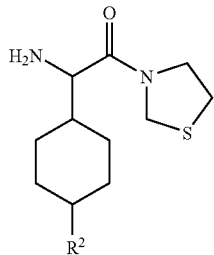

Ig wherein:
R² is defined herein;

and pharmaceutically acceptable salts and individual diastereomers thereof.

Another group of compounds of the present invention include those of formula Ih:

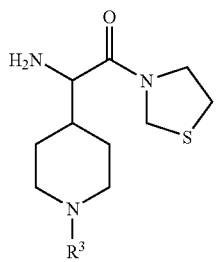

Ih wherein:
R³ is defined herein;

and pharmaceutically acceptable salts and individual diastereomers thereof.

Another group of compounds of the present invention include those of formula Ii:

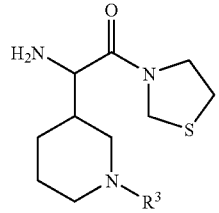

Ii wherein:
R³ is defined herein;

and pharmaceutically acceptable salts and individual diastereomers thereof.

Another group of compounds of the present invention include those of formula Ij:

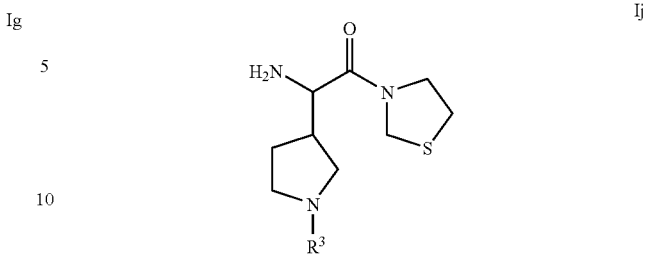

Ij wherein:
R³ is defined herein;

and pharmaceutically acceptable salts and individual diastereomers thereof.

In the present invention it is more preferred that X is selected from —S—, —CH₂—, —CHF— and —CF₂—.

In the present invention it is preferred that R¹ is hydrogen.

In the present invention it is preferred that R² is selected from the group consisting of:
(1) —NR⁴—CO—NR⁵R⁶,
(2) —NR⁴—CO₂R⁶,
(3) —NR⁴—COR⁶, and
(4) —NR⁴—S(O)₂—R⁶.

In the present invention it is even more preferred that R² is selected from the group consisting of:
(1) —NR⁴—CO—NR⁵R⁶,
(2) —NR⁴—CO₂R⁶,
(3) —NR⁴—COR⁶, and
(4) —NR⁴—S(O)₂—R⁶.

In the present invention it is highly preferred that R² is selected from the group consisting of:
(1) —NR⁴—COR⁶, and
(2) —NR⁴—S(O)₂—R⁶.

In the present invention it is preferred that R³ is selected from the group consisting of:
(1) —CO—NR⁵R⁶,
(2) —CO₂R⁶,
(3) —COR⁶, and
(4) —S(O)₂—R⁶.

In the present invention it is more preferred that R³ is selected from the group consisting of:
(1) —CO—NR⁵R⁶,
(2) —COR⁶, and
(3) —S(O)₂—R⁶.

In the present invention it is preferred that R⁴ and R⁵ are independently selected from hydrogen and methyl.

In the present invention it is preferred that the heterocycle is independently selected from: benzodioxanyl, benzoxadiazolyl, benzothiadiazolyl, cinnolinyl, furanyl, imidazolyl, indolyl, isooxazolyl, oxazolyl, pyrazolyl, pyridyl, qunolinyl, quinoxalinyl, tetrahydroimidazolyl, tetrahydroisoquinolinyl, thiazolidinyl, and thienyl.

In the present invention it is preferred that R⁶ is independently selected from:
(1) phenyl and C₁₋₃alkyl-phenyl, wherein the phenyl is unsubstituted or substituted, where the substituents are independently selected from:
(a) halogen,
(b) —OCF₃,
(c) —CF₃,
(d) C₁₋₆alkyl, (e) —O—$C_{1-6}$alkyl, and
(f) phenyloxy,
(2) naphthyl, wherein the naphthyl is unsubstituted or substituted, where the substituents are independently selected from:
(a) halogen,
(b) —$OCF_3$,
(c) —$CF_3$,
(d) $C_{1-6}$alkyl, and
(e) —O—$C_{1-6}$alkyl,
(3) biphenyl, wherein the biphenyl is unsubstituted or substituted, where the substituents are independently selected from:
(a) halogen,
(b) —$OCF_3$,
(c) —$CF_3$,
(d) $C_{1-6}$alkyl, and
(e) —O—$C_{1-6}$alkyl.

In the present invention it is more preferred that $R^6$ is independently selected from:
(1) phenyl, wherein the phenyl is unsubstituted or substituted, where the substituents are independently selected from:
(a) halogen,
(b) —$OCF_3$,
(c) —$CF_3$,
(d) $C_{1-6}$alkyl,
(e) —O—$C_{1-6}$alkyl, and
(f) phenyloxy,
(2) —$CH_2$-phenyl, wherein the phenyl is unsubstituted or substituted, where the substituents are independently selected from:
(a) halogen,
(b) —$OCF_3$,
(c) —$CF_3$,
(d) $C_{1-6}$alkyl,
(e) —O—$C_{1-6}$alkyl, and
(f) phenyloxy,
(2) naphthyl, wherein the naphthyl is unsubstituted or substituted, where the substituents are independently selected from:
(a) halogen,
(b) —$OCF_3$,
(c) —$CF_3$,
(d) $C_{1-6}$alkyl, and
(e) —O—$C_{1-6}$alkyl,
(3) biphenyl, wherein the biphenyl is unsubstituted or substituted, where the substituents are independently selected from:
(a) halogen,
(b) —$OCF_3$,
(c) —$CF_3$,
(d) $C_{1-6}$alkyl, and
(e) —O—$C_{1-6}$alkyl.

In the present invention it is still more preferred that $R^6$ is independently selected from:
(1) phenyl, wherein the phenyl is unsubstituted or substituted, where the substituents are independently selected from:
(a) fluoro,
(b) chloro,
(c) iodo,
(d) —$OCF_3$,
(e) —$CF_3$,
(f) —O—$CH_3$,
(g) methyl,
(h) isopropyl, and
(i) tert-butyl,
(2) —$CH_2$-phenyl, wherein the phenyl is unsubstituted or substituted, where the substituents are independently selected from:
(a) fluoro,
(b) chloro,
(c) iodo,
(d) —$OCF_3$,
(e) —$CF_3$,
(f) —O—$CH_3$,
(g) methyl,
(h) isopropyl, and
(i) tert-butyl,
(2) naphthyl, wherein the naphthyl is unsubstituted or substituted, where the substituents are independently selected from:
(a) fluoro,
(b) chloro,
(c) iodo,
(d) —$OCF_3$,
(e) —$CF_3$,
(f) —O—$CH_3$,
(g) methyl,
(h) isopropyl, and
(i) tert-butyl,
(3) biphenyl, wherein the biphenyl is unsubstituted or substituted, where the substituents are independently selected from:
(a) fluoro,
(b) chloro,
(c) iodo,
(d) —$OCF_3$,
(e) —$CF_3$,
(f) —O—$CH_3$,
(g) methyl,
(h) isopropyl, and
(i) tert-butyl.

The compounds of the instant invention have one asymmetric center at the alpha carbon atom. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the most preferred compounds of this invention are of the trans orientation, i.e. as depicted:

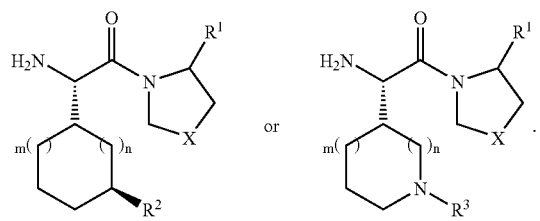

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

As appreciated by those of skill in the art, halo or halogen as used herein are intended to include fluoro, chloro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. A group which is designated as being independently substituted with substituents may be independently substituted with multiple numbers of such substituents. The term "heterocycle" as used herein is intended to include the following groups: benzimidazolyl, benzodioxanyl, benzofuranyl, benzopyrazolyl, benzothiadiazolyl, benzotriazolyl, benzothiophenyl, benzoxadiazolyl, benzoxazolyl, carbazolyl, carbolinyl, chromanyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolinyl, quinoxalinyl, tetrazolyl, thiadiazolyl, thiazolidinyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydroimidazolyl, etrahydroisoquinolinyl, and tetrahydrothienyl.

Exemplifying the invention is the use of the compounds disclosed in the Examples and herein.

Specific compounds within the present invention include a compound which selected from the group consisting of the compounds disclosed in the following Examples and pharmaceutically acceptable salts thereof and individual diastereomers thereof.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutical carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention, as inhibitors of dipeptidyl peptidase-IV enzyme activity may be demonstrated by methodology known in the art. Inhibition constants are determined as follows. A continuous fluorometric assay was employed with the substrate Gly-Pro-AMC, which is cleaved by DP-IV to release the fluorescent AMC leaving group. The kinetic parameters that describe this reaction are as follows: $K_m=50$ µM; $k_{cat}=75$ s$^{-1}$; $k_{cat}/K_m=1.5\times10^6$ M$^{-1}$ s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. Unless otherwise indicated, the enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants were never more than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes is humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP, glucagon). Inactivation of these peptides by DP-IV may also play a role in glucose homeostasis.

The DP-IV inhibitors of the present invention therefore have utility in the treatment of type II diabetes and in the treatment and prevention of the numerous conditions that often accompany Type II diabetes, including metabolic syndrome X, reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (Am. J. Physiol. 277, R910–R916 (1999)). ICV administration of GLP-1 in rats and mice also has profound effects on food intake (Nature Medicine 2, 1254–1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (Nature Medicine 6, 802–807 (2000)).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRH is efficiently cleaved in vitro to generate the inactive product GRH[3-44] (BBA 1122, 147–153 (1992)); (2) GRH is rapidly degraded in plasma to GRH[3-44]; this is prevented by the DP-IV inhibitor diprotin A; and (3) GRH[3-44] is found in the plasma of a human GRH transgenic pig (J. Clin. Invest. 83, 1533–1540 (1989)). Thus DP-IV inhibitors may be useful for the same spectrum of indications which have been considered in the case of Growth Hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (Regulatory Peptides 90, 27–32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosphonate), an irreversible inhibitor of DP-IV, was shown to double cardiac allograft survival in rats from day 7 to day 14 (Transplantation 63, 1495–1500 (1997)). DP-IV inhibitors have been tested in collagen and alkyldiamine-induced arthritis in rats and showed a statistically significant attenuation of hind paw swelling in this model (Int. J. Immunopharmacology 19, 15–24 (1997), Immunopharmacology 40, 21–26 (1998)). DP-IV is upregulated in a number of autoimmune diseases including rheumatoid arthritis, multiple sclerosis, Graves' disease, and Hashimoto's thyroiditis (Immunology Today 20, 367–375 (1999)).

HIV Infection: DP-IV inhibition may be useful for the treatment or prevention of HIV infection or AIDS because a number of chemokines which inhibit HIV cell entry are potential substrates for DP-IV (Immunology Today 20, 367–375 (1999)). In the case of SDF-1alpha, cleavage decreases antiviral activity (PNAS 95, 6331–6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m \sim 10^6$ $M^{-1}$ $s^{-1}$ or greater. In an electric shock jump test model of analgesia in rats, a DP-IV inhibitor showed a significant effect that was independent of the presence of exogenous endomorphin-2 (Brain Research 815, 278–286 (1999)).

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (J. Exp. Med. 190, 301–305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (Eur. J. Clin. Chem. Clin. Biochem 30, 333–338 (1992)).

Sperm Motility/Male Contraception: DP-IV inhibition may be useful for the altering sperm motility and for male contraception because in seminal fluid, prostatosomes, prostate derived organelles important for sperm motility, possess very high levels of DP-IV activity (Eur. J. Clin. Chem. Clin. Biochem 30, 333–338 (1992)).

Gingivitis: DP-IV inhibition may be useful for the treatment of gingivitis because DP-IV activity was found in gingival crevicular fluid and in some studies correlated with periodontal disease severity (Arch. Oral Biol. 37, 167–173 (1992)).

Osteoporosis: DP-IV inhibition may be useful for the treatment or prevention of osteoporosis because GIP receptors are present in osteoblasts.

The subject compounds are further useful in a method for the prevention or treatment of the aforementioned diseases, disorders and conditions in combination with other agents.

Compounds of Formula I may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas such as tolbutamide and glipizide, meglitinide, and related materials;

(e) α-glucosidase inhibitors (such as acarbose);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP and GIP mimetics such as those disclosed in WO00/58360;

(i) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as for example beta-sitosterol, (vii) acyl CoA:cholesterol acyltransferase inhibitors, such as for example avasimibe, and (viii) anti-oxidants, such as probucol;

(j) PPARδ agonists, such as those disclosed in WO97/28149;

(k) antiobesity compounds such as fenfluramine, dexfenfluramine, phentermine, sibutramine, orlistat, neuropeptide Y5 inhibitors, and β$_3$ adrenergic receptor agonists;

(l) an ileal bile acid transporter inhibitor; and (m) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and anti-obesity compounds.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

In one embodiment of the present invention, the compounds (Ia), where $R^1$ is defined as hydrogen, can be prepared from alpha amino acid intermediates such as those of formula II and heterocyclic intermediates such as those of formula III using standard peptide coupling conditions followed by deprotection. The preparation of intermediates II is described in the following schemes.

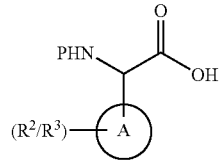

II

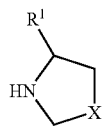

III where A is cyclohexyl, cyclopentyl, piperidinyl or pyrrolidinyl, and $R^1$, $R^2$, $R^3$ and X are as defined above and P is a suitable nitrogen protecting group such as tert-butoxycarbonyl, benzyloxycarbonyl, or 9-fluorenylmethoxycarbonyl.

SCHEME 1

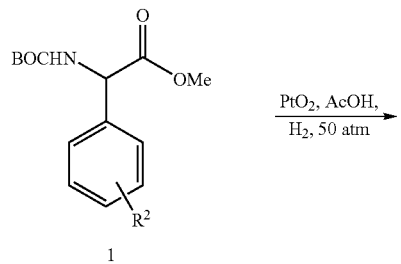

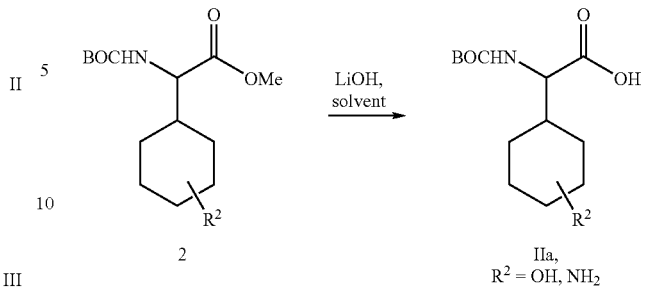

Compounds IIa, where A is a cyclohexyl ring and $R^2$ is an alcohol or amino group are known in the literature or may be conveniently prepared by a variety of methods familiar to those skilled in the art. One route is illustrated in Scheme 1. Ester 1, which may be commercially available or readily prepared from the corresponding amino acid by protection using, for example di-tert-butyloxydicarbonate, and esterification in methanol or ethanol containing an acid such as hydrochloric acid, is subjected to catalytic hydrogenation using a catalyst such as platinum oxide in a solvent such as acetic acid at a pressure of up to 50 psi for a time of 2 to 16 hours to the give cyclohexyl analog 2. The ester functionality in compound 2 can be removed to yield the carboxylic acid IIa. In the case of an ester such as methyl or ethyl, this is achieved by saponification using a base such as aqueous lithium hydroxide in a polar solvent such as tetrahydrofuran, methanol or a mixture of similar solvents. As will be understood by those skilled in the art, for the preparation of enantiomerically pure alpha amino acids II, enantiomerically pure alpha amino acids 1 may be used. Related routes to these compounds can be found in the following references: Nutt et al., Peptides: Structure and Function, Proceed. of the 9th Amer. Pept. Symp., eds C. Deber et al., Pierce Chemical Co. Rockford, Ill, 441 (1985), and Banfi et al., *Syn. Commun.,* 19, 1787–1799 (1989).

SCHEME 2

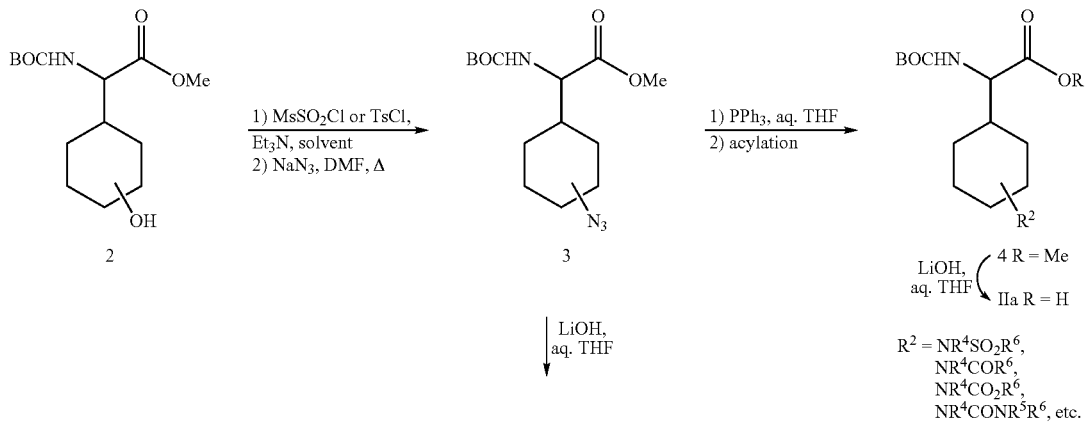

-continued

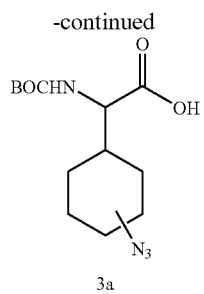

3a

In most cases, the reduction product 2 from the reactions described in Scheme 1 will be further modified, by the manipulation of $R^2$. These manipulations may include, but are not limited to substitution, reduction, oxidation, alkylation, acylation, and hydrolysis reactions which are commonly known to those skilled in the art. One such example is shown in Scheme 2. Alcohol 2 ($R^2/R^3$=OH) is sulfonylated with a sulfonyl chloride, for example, methanesulfonyl choride or toluenesulfonyl chloride in a solvent such as methylene chloride in the presence of a base, generally triethylamine. The sulfonate ester is then displaced with an azide group, using a reagent such as lithium or sodium azide in a polar solvent, for example, dimethylformamide (DMF), for 16 to 100 hours at 25–60° C. The azide 3 can be reduced to the amine and acylated to give compound 4. The reduction can be effected with, for example, triphenyl phosphine in aqueous tetrahydrofuran for 3 to 24 hours at a temperature of 25 to 50° C., or by catalytic hydrogenation using a palladium catalyst in a solvent such as methanol, ethyl acetate or a mixture of such solvents. Treatment of the amine with an acylating agent such as a sulfonyl chloride, acid chloride, isocyanate, or carbamoyl chloride gives ester 4 which is converted to acid IIa. In the case of an ester such as methyl or ethyl, this is achieved by saponification using a base such as aqueous lithium hydroxide in a polar solvent such as tetrahydrofuran, methanol or a mixture of similar solvents. Alterpatively, the ester functionality on azide 3 can be removed in a similar fashion to that described above to yield 3a with the amino group protected as the azide for the coupling reaction with heterocycle III.

An alternate route to intermediates II is shown in Scheme 3. Ketones 5, which are commercially available, known in the literature, or may be conveniently prepared by a variety of methods familiar to those skilled in the art, will undergo a Horner-Emmons coupling with phosphonate 6, where P is a suitable protecting group such as tert-butoxycarbonyl or benzyloxycarbonyl, using a hindered base, generally 1,8-diazabicylo[5.4.0]undec-7-ene (DBU) or potassium tert-butoxide in an inert solvent such as methylene chloride at −80–25° C. for 2 to 72 hours. Reagents such as 6 are commercially available, or can be synthesised as described in Schmidt et al., *Synthesis*, 53 (1984). The resultant double bond can then be reduced to give ester 7 by, for example catalytic hydrogenation which is carried out using a catalyst such as palladium on carbon or platinum oxide in a polar protic solvent, for example acetic acid or methanol which may contain a catalytic quantity of mineral acid such as hydrochloric acid, at pressures of up to 50 psi. Enantioselective reductions of the double bond can be carried out using procedures described in Burk et al., *J. Am. Chem. Soc.*, 117, 9375, (1995). Carboxylic acid II is then prepared by removal of the ester. In the case of an ester such as methyl or ethyl, this is achieved by saponification as described above.

In some cases, the reduction product 7 from the reactions described in Scheme 3 will be further modified, by the manipulation of $R^2/R^3$ prior to formation of carboxylic acid II. These manipulations may include, but are not limited to substitution, reduction, oxidation, alkylation, acylation, and hydrolysis reactions which are commonly known to those skilled in the art.

SCHEME 3

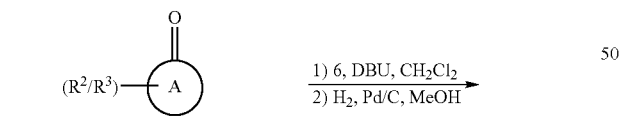

5
6 = (MeO)$_2$POCH(CO$_2$Me)NHP

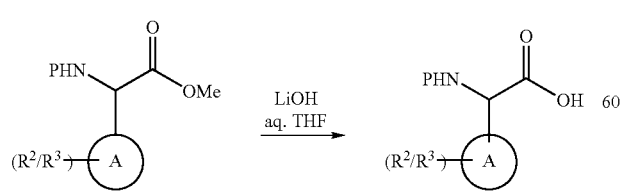

SCHEME 4

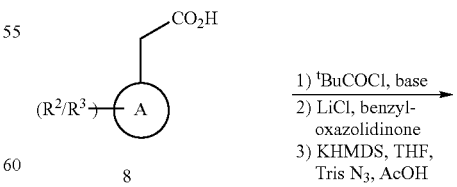

8

1) $^t$BuCOCl, base
2) LiCl, benzyl-oxazolidinone
3) KHMDS, THF, Tris N$_3$, AcOH

SCHEME 5

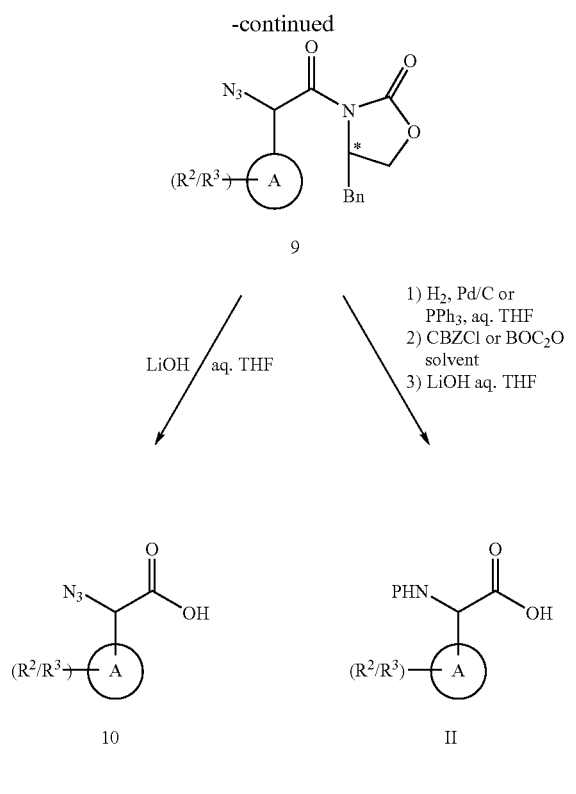

An alternate route to intermediates II is shown in Scheme 4 and described in Evans et al., *J. Am. Chem. Soc.*, 112, 4011, (1990) and Ho et. al., *J. Org. Chem.*, 60, 2271, (1995). Carboxylic acids 8 are commercially available, known in the literature, or may be conveniently prepared by a variety of methods familiar to those skilled in the art. Carboxylic acid 8 can be activated by treatment with, for example, thionyl chloride or an acid chloride such as pivaloyl chloride and a base such as triethylamine. This is then converted to azido compound 9, by treatment with either enantiomer of 4-benzyloxazolidin-2-one and lithium chloride in a solvent such as THF, followed by reaction with an alkali metal base, generally potassium hexamethyldisilazide in a polar solvent such as THF at −80–25° C. and trisyl azide. The reaction is quenched under acidic conditions, usually with acetic acid. Reduction of the azido group in 9 can be effected with, for example, triphenyl phosphine in aqueous tetrahydrofuran for 3 to 24 hours at a temperature of 25–50° C., or by catalytic reduction using a palladium catalyst in a solvent such as methanol, ethyl acetate or a mixture of such solvents to give an amino group which is protected with a suitable protecting group such as tert-butoxycarbonyl or benzyloxycarbonyl. Intermediate II is isolated by hydrolysis of the oxazolidinone. This can be effected by using a base such as aqueous lithium hydroxide in a polar solvent such as tetrahydrofuran, methanol or a mixture of similar solvents. Alternatively, the chiral auxiliary on azide 9 can be removed in a similar fashion to that described above to yield 10 with the amino group protected as the azide.

A route to intermediates IIb where A is a cycloalkyl ring with a substituent in the 3-position is shown in Scheme 5 and further described in Eustache et al., *Bioorg. Med. Chem. Lett.*, 8, 2961, (1996) and Schollkopf et al., *Angew. Chem. Int. Ed. Engl.*, 27, 1194 (1988). Addition of either enantiomer of bislactim-ether cuprate 11 to cyclic enone 12 in THF at less than −30° C. for 4–16 hours results in formation of compound 13. The keto group can be modified, for example by reduction to the alcohol using an alkali metal hydride such as sodium borohydride in a polar solvent, generally ethanol. Further manipulations may also be performed which may include, but are not limited to substitution, reduction, oxidation, alkylation, acylation, and hydrolysis reactions which are commonly known to those skilled in the art. Removal of the chiral auxiliary can be achieved by treatment with a dilute mineral acid, such as hydrochloric in a polar solvent, for example THF. Protection of the thus formed amine with a suitable protecting group such as tert-butoxycarbonyl or benzyloxycarbonyl yields ester 14 which can converted to intermediate IIb. This can be effected by using a base such as aqueous lithium hydroxide in a polar solvent such as tetrahydrofuran, methanol or a mixture of similar solvents.

In some cases, the product 14 from the reactions described in Scheme 5 will be further modified, by the manipulation of $R^2$ prior to formation of carboxylic acid II. These manipulations may include, but are not limited to substitution, reduction, oxidation, alkylation, acylation, and hydrolysis reactions which are commonly known to those skilled in the art.

in Scheme 6. The protecting group is then removed with, for example, trifluoroacetic acid in the case of Boc or hydrobromic acid in acetic acid in the case of Cbz to give the desired amine 16. The product is purified from unwanted side products by recrystallization, trituration, preparative thin layer chromatography, flash chromatography on silica gel as described by W. C. Still et al, *J. Org. Chem.*, 43, 2923, (1978), or HPLC. Compounds which are purified by HPLC may be isolated as the corresponding salt. Purification of intermediates is achieved in the same manner.

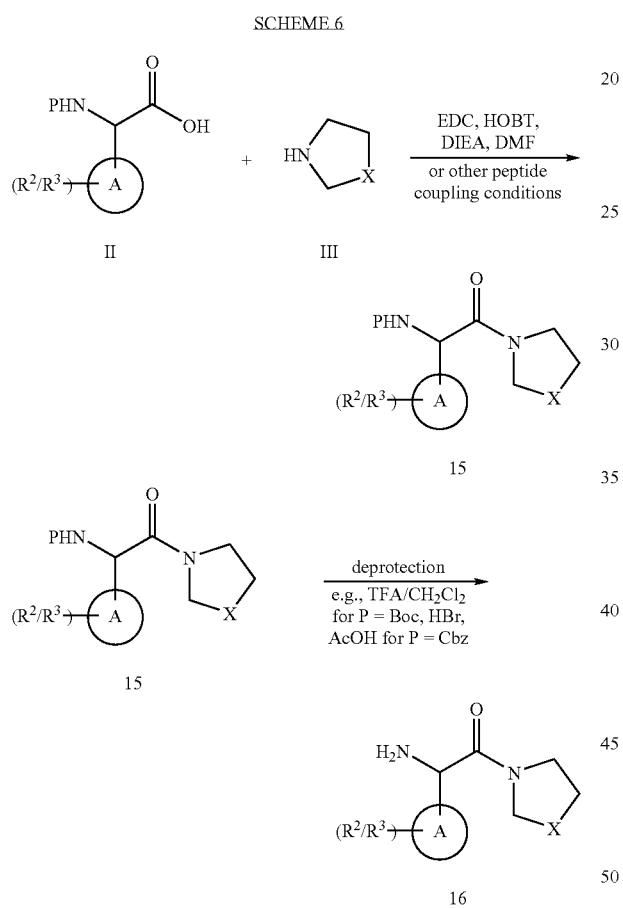

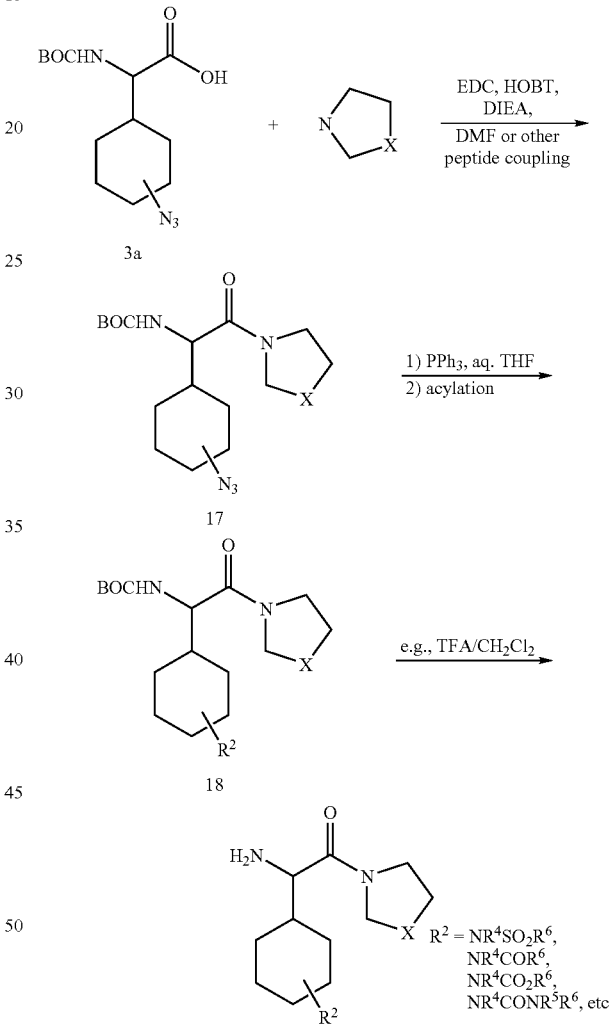

Intermediates III, are commercially available, known in the literature or may be conveniently prepared by a variety of methods familiar to those skilled in the art. One common route, when X=CHF or $CF_2$, is described in Augustyns et. al., *Eur. J. Med. Chem.*, 32, 301, (1997) or Giardina et. al., *Synlett.*, 55, (1995).

Intermediates II and III are coupled under standard peptide coupling conditions, for example, using 1-ethyl-3-(3-dimethylaminopropyl)-carbodiimide (EDC), 1-hydroxybenzotriazole (HOBT), and a base, generally diisopropylethylamine, in a solvent such as N,N-dimethylformamide (DMF) or methylene chloride for 3 to 48 hours at ambient temperature to provide intermediate 15 as shown In some cases the intermediate 15 from the coupling reaction described in Scheme 6 may be further modified before removal of the protecting group, for example, by manipulation of substituents on $R^2/R^3$. These manipulations may include, but are not limited to, substitution, reduction, oxidation, alkylation, acylation, and hydrolysis reactions which are commonly known to those skilled in the art. One such example using intermediate 3a is illustrated in Scheme 7. The azide 3a can be coupled as described above to give amide 17, which can then be reduced to the amine and acylated to give compound 18. The reduction can be effected with, for example, triphenyl phosphine in aqueous tetrahydrofuran for 3 to 24 hours at a temperature of 25 to 50° C., or by catalytic reduction using a palladium catalyst in a solvent such as methanol, ethyl acetate or a mixture of such solvents. Treatment of the amine with an acylating agent such as a sulfonyl chloride, acid chloride, isocyanate, or carbamoyl chloride gives amide 18. The protecting group is then removed with, for example, trifluoroacetic acid to give the desired amine.

SCHEME 8

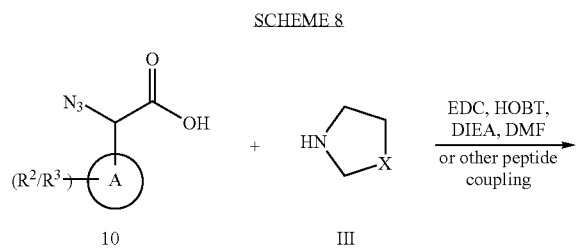

Intermediate 10 and heterocycle III can also be coupled under standard peptide coupling conditions, for example, using EDC, HOBt, and a base, generally diisopropylethylamine, in a solvent such as DMF or methylene chloride for 3 to 48 hours at ambient temperature to provide 19 as shown in Scheme 8. The azide 19 can then be reduced to the amine to give compound I. The reduction can be effected with, for example, triphenyl phosphine in aqueous tetrahydrofuran for 3 to 24 hours at a temperature of 25 to 50° C., or by catalytic reduction using a palladium catalyst in a solvent such as methanol, ethyl acetate or a mixture of such solvents. In some cases the intermediate 19 from the coupling reaction described in Scheme 8 may be further modified before reduction of the azide, for example, by manipulation of substituents on $R^2/R^3$. These manipulations may include, but are not limited to, substitution, reduction, oxidation, alkylation, acylation, and hydrolysis reactions which are commonly known to those skilled in the art.

In a further embodiment of the invention, where $R^1$ is defined as nitrile, the compounds (I) can be prepared from alpha amino acid intermediates such as those of formula II, whose synthesis has been described above, and carboxamide intermediates of formula IV where X is as defined above.

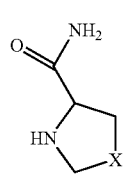

IV

Compounds IV are commercially available, known in the literature or may be conveniently prepared by a variety of methods familiar to those skilled in the art.

SCHEME 9

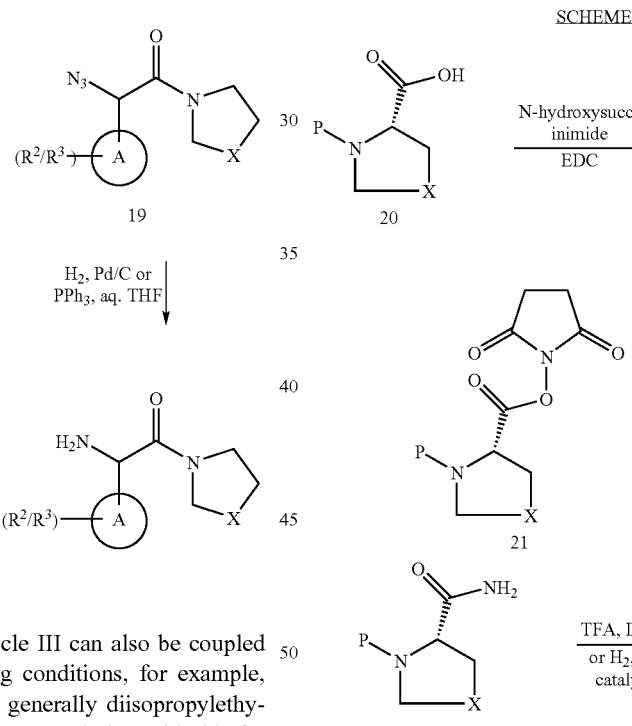

One common route to compounds IV is illustrated in Scheme 9 and involves treatment of carbamate derivative 20 with N-hydroxysuccinimide and EDC or other suitable coupling agent in a solvent such as dichloromethane for 1 to 16 hours. The resulting product 21 is then treated with a base, for example, aqueous ammonium hydroxide in a solvent such as dioxane. Removal of the protecting group as described above gives the intermediate IV. Carbamate derivatives 20 are commercially available, known in the literature or may be prepared by a variety of methods familiar to those skilled in the art. For example, when X=CHF or CF$_2$, synthesis of the methyl ester of 20 is described in Demange et. al., *Tetrahedron Lett.*, 39, 1169, (1998).

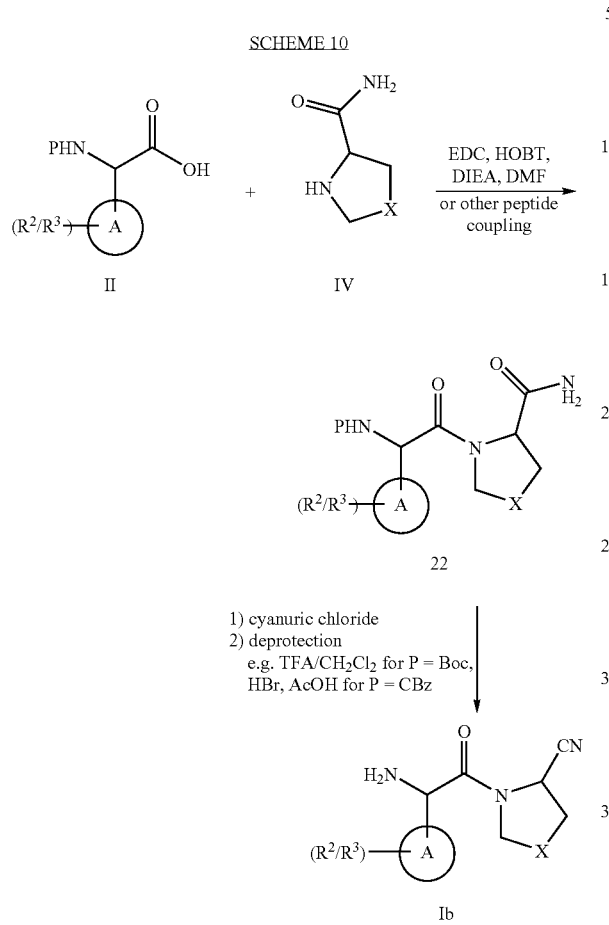

Intermediates II and IV are coupled under standard peptide coupling conditions, for example, using EDC, HOBt, and a base, generally diisopropylethylamine, in a solvent such as DMF or methylene chloride for 3 to 48 hours at ambient temperature to provide intermediate 22 as shown in Scheme 10. This is then treated with a dehydrating agent such as cyanuric chloride in a polar solvent, for example, dimethylformamide for 1 to 16 hours at 0 to 50° C. to provide the nitrile. The protecting group is then removed with, for example, trifluoroacetic acid in the case of Boc or hydrobromic acid in acetic acid in the case of Cbz to give the desired amine Ib. In some cases the intermediate 22 from the coupling reaction described in Scheme 10 may be further modified before formation of the nitrile, for example, by manipulation of substituents on R$^2$/R$^3$. These manipulations may include, but are not limited to, substitution, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided for the purpose of further illustration only and are not intended to be limitations on the disclosed invention.

EXAMPLE 1

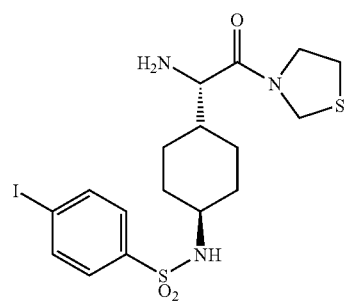

Step A. Methyl cis-(2S)-[(tert-butoxycarbonyl)amino](4-hydroxycyclohexyl)ethanoate To a solution of 20 mL (230 mmol) of acetyl chloride in 400 mL of methanol at 0° C. was added 20 g (120 mmol) of (S)-4-hydroxyphenylglycine. The mixture was stirred at ambient temperature for 16 h, heated at 40° C. for 2 h, cooled and concentrated in vacuo. Water was added and the mixture was extracted three times with methylene chloride. The combined organic phase was washed with brine, dried over magnesium sulfate, and concentrated in vacuo to give the crude methyl ester. This material was dissolved in 400 mL of methylene chloride and 28.8 g (132 mmol) of di-tert-butyl dicarbonate, and 31.4 mL (180 mmol) of diisopropylethyl-amine (DIEA) was added. The mixture was stirred at ambient temperature for 20 h, concentrated in vacuo, and dissolved in 400 mL of ethyl acetate. The organic phase was washed with sequentially with saturated sodium bicarbonate solution, water, and brine, dried over magnesium sulfate, and concentrated in vacuo. The crude solid was triturated with 200 mL of 1:4 ether:hexane to give 30 g of the Boc carbamate which was dissolved in 300 mL of acetic acid. To the solution was added 2.2 g of platinum (IV) oxide and the reaction was shaken under an atmosphere of hydrogen (48 psi) for 2 h, filtered and concentrated in vacuo. The crude material was dissolved in ethyl acetate and washed sequentially with saturated sodium bicarbonate solution, water, and brine, dried over magnesium sulfate, and concentrated in vacuo. Purification by flash chromatography (silica gel, 20 to 40% ethyl acetate in hexanes) afforded 8.83 g of the title compound. $^1$H NMR (400 MHz, CDCl$_3$) δ 5.05 (bd, 1H, J=12 Hz), 4.33–4.27 (m, 1H), 4.05 (bs, 1H), 3.78 (s, 3H), 1.89–1.78 (m, 2H), 1.63–1.38 (m, 16H). Continued elution gave 3.50 g of methyl trans-(2S)-[(tert-butoxycarbonyl)amino](4-hydroxycyclohexyl)ethanoate. $^1$H NMR (400 MHz, CDCl$_3$) δ 5.04 (bd, 1H, J=12 Hz), 4.30–4.23 (m, 1H), 3.78 (s, 3H), 3.59–3.51 (m, 1H), 2.08–2.00 (m, 2H), 1.79–1.50 (m, 3H), 1.43 (s, 9H), 1.33–1.04 (m, 4H).

Step B. Methyl trans-(2S)-[(tert-butoxycarbonyl)amino](4-azidocyclohexyl)ethanoate To a solution of 9.76 g (34 mmol) of methyl cis-(2S)-[(tert-butoxycarbonyl)amino](4-hydroxycyclohexyl)ethanoate in 150 mL of methylene chloride at 0° C. was added 3.94 mL (50.9 mmol) of methanesulfonyl chloride and 11.8 mL (67.9 mmol) of diisopropylethylamine (DIEA). The mixture was stirred at ambient temperature for 3 h, concentrated in vacuo, and diluted with ethyl acetate. The organic phase was washed with saturated aqueous sodium bicarbonate solution, brine, dried over magnesium sulfate and the solvent removed in vacuo to yield the crude methanesulfonate which was immediately dissolved in 100 mL of dimethylformamide (DMF). To this solution was added 5.0 g (102 mmol) of lithium azide and the reaction was heated at 60° C. for 16 h, concentrated in vacuo, and partitioned between ethyl acetate and water. The organic phase was washed with water, brine, dried over magnesium sulfate, and concentrated in vacuo. Purification by flash chromatography (silica gel, 50% ethyl acetate in hexanes) afforded 7.7 g of the title compound. $^1$H NMR (400 MHz, CDCl$_3$) δ 5.03 (bd, 1H, J=12 Hz), 4.33–4.23 (m, 1H), 3.77 (s, 3H), 3.25–3.18 (m, 1H), 2.16–2.03 (m, 2H), 1.82–1.63 (m, 3H), 1.43 (s, 9H), 1.42–1.15 (m, 4H).

Step C. tert-Butyl trans-(1S)-1-(4-aminocyclohexyl)-2-oxo-2-(1,3-thiazolidin-3-yl)ethyl-carbamate To a solution of 3.45 g (11 mmol) of methyl trans-(2S)-[(tert-butoxycarbonyl)amino](4-azidocyclohexyl)ethanoate in 110 mL of a 3:2:1 mixture of tetrahydrofuran:methanol:water was added 1.39 g of lithium hydroxide. The solution was stirred at ambient temperature for 16 h, the solvent removed in vacuo, the aqueous solution was acidified with 2N hydrochloric acid and extracted three times with ethyl acetate. The combined organic phase was washed with brine, dried over magnesium sulfate, and concentrated in vacuo to give 3.06 g of crude carboxylic acid. This product was dissolved in 100 mL of DMF and to the solution was added 0.81 mL (10.2 mmol) of thiazolidine, 1.97 g (10.2 mmol) of 1-ethyl-3-(3-dimethylamino-propyl)-carbodiimide (EDC), and 1.39 g (10.2 mmol) of 1-hydroxybenzotriazole hydrate. The mixture was stirred for 16 h and diluted with ethyl acetate. The organic phase was washed with water, dilute hydrochloric acid, saturated aqueous sodium bicarbonate solution, water, brine, dried over magnesium sulfate and the solvent removed in vacuo to yield 3.86 g of the desired azide. This material was dissolved in 82.5 mL of a 10:1 mixture of tetrahydrofuran:water, 2.97 g (11.3 mmol) of triphenylphosphine was added and stirring was continued at ambient temperature for 16 h. The reaction mixture was concentrated in vacuo and purified by flash chromatography (silica gel, 2–10% methanol in methylene chloride, containing 1% concentrated ammonium hydroxide) to afford 2.05 g of the title compound as a white foam. $^1$H NMR (400 MHz, CD$_3$OD) δ 4.63–4.48 (d, 2H), 4.21–4.06 (m, 1.5H), 3.83–3.67 (m, 1.5H), 3.13 (t, 1H, J=6 Hz), 3.03 (t, 1H, J=6 Hz), 2.61–2.55 (m, 1H), 1.93–1.82 (m, 3H), 1.66–1.60 (m, 2H), 1.41 (s, 9H), 1.23–1.07 (m, 4H).

Step D. N-{4-[(1S)-1-amino-2-oxo-2-(1,3-thiazolidin-3-yl)ethyl]cyclohexyl}-4-iodo-benzenesulfonamide To a solution of 50 mg (0.139 mmol) of tert-butyl trans-(1S)-1-(4-aminocyclohexyl)-2-oxo-2-(1,3-thiazolidin-3-yl)ethyl-carbamate in 1 mL of methylene chloride was added 53 mg (0.175 mmol) of pipsyl chloride, and 0.022 mL (0.27 mmol) of pyridine, and the reaction was stirred at ambient temperature for 16 h. The solvent was removed in vacuo and the product purified by preparative thin layer chromatography (TLC) (silica gel, 5:95 methanol:methylene chloride) afforded 51 mg of the title compound as is Boc carbamate. Deprotection was effected by treatment with 2 mL of a 1:1 mixture of trifluoroacetic acid:methylene chloride at ambient temperature for 2 h, followed by concentration in vacuo and removal of the excess trifluoroacetic acid by azeotropic distillation with methylene chloride. Purification by preparative TLC (silica gel, 9:1:90 methanol:concentrated ammonium hydroxide:methylene chloride) afforded 37 mg of the title compound. $^1$H NMR (400 MHz, CD$_3$OD) δ 7.94 (d, 2H, J=8 Hz), 7.58 (d, 2H, J=8 Hz), 4.64–4.62 (m, 0.45H), 4.58–4.52 (m, 1H), 4.47–4.43 (m, 0.55H), 3.91–3.64 (m, 2H), 3.41 (d, 0.45H, J=7 Hz), 3.37 (d, 0.55H, J=7 Hz), 3.07 (t, 1.1H, J=6 Hz), 3.02 (t, 0.9H, J=6 Hz), 3.00–2.92 (m, 1H), 1.84–1.72 (m, 3H), 1.59–1.52 (m, 1H), 1.48–1.38 (m, 1H), 1.23–1.10 (m, 3H), 1.09–0.97 (m, 1H).

EXAMPLE 2

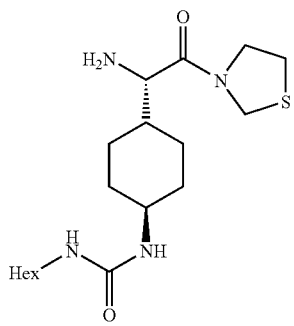

N-{4-[(1S)-1-amino-2-oxo-2-(1,3-thiazolidin-3-yl)ethyl]cyclohexyl}-N'-hexylurea 317 mg (1 mmol) of trans-(2S)-[(tert-butoxycarbonyl)amino](4-azidocyclohexyl)ethanoate was reduced using an identical procedure to that described in Example 1, Step C to yield 290 mg of trans-(2S)-[(tert-butoxycarbonyl)amino](4-aminocyclohexyl)ethanoate. To a solution of 30 mg (0.1 mmol) of trans-(2S)-[(tert-butoxycarbonyl)amino](4-aminocyclohexyl)ethanoate in 1 mL of methylene chloride at 0° C. was added 0.018 mL (0.125 mmol) of hexyl isocyanate and 0.044 mL (0.25 mmol) of diisopropylethylamine (DIEA). The mixture was stirred at ambient temperature for 16 h, concentrated in vacuo, and diluted with ethyl acetate. The organic phase was washed with saturated aqueous sodium bicarbonate solution, brine, dried over magnesium sulfate and the solvent removed in vacuo to yield methyl trans-(2S)-[(tert-butoxycarbonyl)amino](4-{[(hexylamino)carbonyl]amino}cyclohexyl)-ethanoate which was used without further purification. To this material, dissolved in 1 mL of THF, was added 21 mg (0.5 mmol) of lithium hydroxide in 1 mL of water and the reaction was stirred for 16 h and concentrated in vacuo. The aqueous solution was acidified with 2N hydrochloric acid and extracted three times with ethyl acetate. The combined organic phase was washed with brine, dried over magnesium sulfate, and concentrated in vacuo to give the carboxylic acid which was dissolved in 1 mL of dimethylformamide (DMF). To this was added 0.008 mL (0.1 mmol) of thiazolidine, 23 mg (0.12 mmol) of 1-ethyl-3-(3-dimethylaminopropyl)-carbodiimide (EDC), 21 mg (0.15 mmol) of 1-hydroxybenzotriazole hydrate (HOBT), and 0.042 mL (0.25 mmol) of diisopropylethylamine (DIEA). The mixture was stirred for 16 h and diluted with ethyl acetate. The organic phase was washed with water, saturated aqueous sodium bicarbonate solution, water, brine, dried over magnesium sulfate and the solvent removed in vacuo to yield 53 mg The product was deprotected as described in Example 1, Step D, to give 22 mg of the title compound. $^1$H NMR (400 MHz, CD$_3$OD) δ 4.70–4.66 (m, 0.45H), 4.61–4.57 (m, 1H), 4.5–4.46 (m, 0.55H), 3.93–3.86 (m, 0.55H), 3.83–3.71 (m, 1.45H), 3.46 (d, 0.45H, J=7 Hz), 3.42–3.35 (m, 1.55H), 3.16–3.02 (m, 4H), 1.98–1.90 (m, 3H), 1.64–1.58 (m, 1H), 1.56–1.39 (m, 3H), 1.39–1.23 (m, 7H), 1.23–1.06 (m, 3H), 0.95–0.87 (m, 3H).

EXAMPLE 3

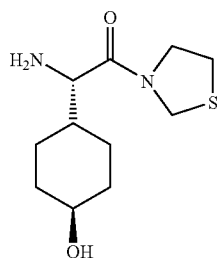

Trans-4-[(1S)-1-amino-2-oxo-2-(1,3-thiazolidin-3-yl)ethyl]cyclohexanol 3.5 g (12.2 mmol) of methyl trans-(2S)-[(tert-butoxycarbonyl)-amino](4-hydroxycyclohexyl)-ethanoate was converted to 3.34 g of tert-butyl trans-(1S)-1-(4-hydroxycyclohexyl)-2-oxo-2-(1,3-thiazolidin-3-yl)ethyl-carbamate using the procedures outlined in Example 1, Step C. $^1$H NMR (400 MHz, CD$_3$OD, mixture of rotamers) δ 4.65–4.47 (m, 1.5H), 4.19–4.05 (m, 1.5H), 3.55–3.40 (m, 1H), 3.17–3.03 (m, 2H), 2.00–1.83 (m, 3H), 1.70–1.58 (m, 2H), 1.45–1.38 (m, 9H), 1.30–1.08 (m, 4H). A portion of this material was deprotected as described in Example 1, Step D to give the title compound. $^1$H NMR (400 MHz, CD$_3$OD, mixture of rotamers) δ 4.65–4.63 (m, 0.5H), 4.61–4.57 (m, 1H), 4.50–4.44 (m, 0.5H), 3.93–3.85 (m, 0.5H), 3.82–3.71 (m, 1.5H), 3.50–3.38 (m, 2H), 3.15–3.02 (m, 2H), 2.01–1.83 (m, 3H), 1.63–1.59 (m, 1H), 1.55–1.45 (m, 1H), 1.30–1.05 (m, 4H).

EXAMPLE 4

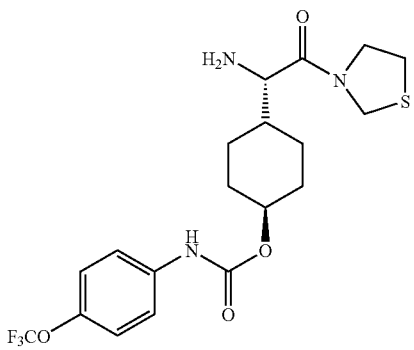

Trans-4-[(1S)-1-amino-2-oxo-2-(1,3-thiazolidin-3-yl)ethyl]cyclohexyl4-(trifluoro-methoxy)phenylcarbamate To a solution of 51 mg (0.15 mmol) of tert-butyl trans-(1S)-1-(4-hydroxycyclohexyl)-2-oxo-2-(1,3-thiazolidin-3-yl)ethyl-carbamate in 3 mL of methylene chloride was added 0.0226 mL (0.15 mmol) of 4-trifluoromethoxy-phenylisocyanate and 0.0836 mL (0.6 mmol) of triethylamine. The reaction was stirred at ambient temperature for 16 h, concentrated in vacuo, and purified by preparative TLC (silica gel, 3:97 methanol:methylene chloride) to afford 19 mg of the title compound as is Boc carbamate. Deprotection was effected by treatment with 2 mL of a 1:1 mixture of trifluoroacetic acid:methylene chloride at ambient temperature for 2 h, followed by concentration in vacuo and removal of the excess trifluoroacetic acid by azeotropic distillation with methylene chloride. Purification by preparative TLC (silica gel, 4.5:0.5:95 methanol:concentrated ammonium hydroxide:methylene chloride) afforded 12.6 mg of the title compound. $^1$H NMR (500 MHz, CD$_3$OD, mixture of rotamers) δ 7.48 (d, 2H, J=8 Hz), 7.17 (d, 2H, J=8 Hz), 4.69 (d, 0.45H, J=8 Hz), 4.63–4.57 (m, 2H), 4.50 (d, 0.55H, J=8 Hz), 3.97–3.90 (m, 0.55H), 3.83–3.72 (m, 1.45H), 3.52 (d, 0.45H, J=7 Hz), 3.46 (d, 0.55H, J=7 Hz), 3.13 (t, 1.1H, J=6 Hz), 3.04 (t, 0.9H, J=6 Hz), 2.17–2.05 (m, 2H), 2.00–1.95 (m, 1H), 1.73–1.68 m, 1H), 1.62–1.54 (m, 1H), 1.43–1.30 (m, 3H), 1.29–1.19 (m, 1H).

EXAMPLE 5

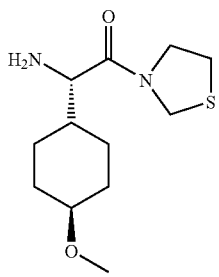

Trans-(1S)-1-(4-methoxycyclohexyl)-2-oxo-2-(1,3-thiazolidin-3-yl)ethanamine

To a solution of 51 mg (0.25 mmol) of tert-butyl trans-(1S)-1-(4-hydroxycyclohexyl)-2-oxo-2-(1,3-thiazolidin-3-yl)ethyl carbamate in 0.25 mL of methyl iodide was added 28 mg (0.5 mmol) of potassium hydroxide, and stirring was continued at ambient temperature for 20 h. The mixture was partitioned between ethyl acetate and water, and the organic phase washed with brine, dried over magnesium sulfate and the solvent removed in vacuo to yield 34 mg of crude product. Purification by preparative TLC (silica gel, ethyl acetate) afforded 8 mg of the title compound as its Boc carbamte. Deprotection was effected by treatment with 4N hydrogen chloride in dioxane at ambient temperature for 2 h, followed by concentration in vacuo. Purification by preparative TLC (silica gel, 10:90 methanol:ethyl acetate) afforded 3 mg of the title compound. $^1$H NMR (500 MHz, CD$_3$OD, mixture of rotamers) δ 4.65–4.63 (m, 0.5H), 4.61–4.57 (m, 1H), 4.49–4.44 (m, 0.5H), 3.94–3.88 (m, 0.5H), 3.82–3.63 (m, 1.5H), 3.50–3.40 (m, 1H), 3,34 (s, 3H), 3.17–3.02 (m, 3H), 2.17–2.03 (m, 2H), 1.93–1.88 (m, 1H), 1.66–1.62 (m, 1H), 1.57–1.46 (m, 1H), 1.32–1.03 (m, 4H).

EXAMPLE 6

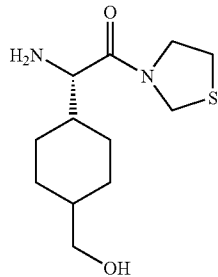

Step A. 4-Hydroxymethylcyclohexanol

To a solution of 10 g (0.058 mol) of ethyl 2-(4-hydroxycyclohexyl)-acetate in 250 mL of anhydrous ethyl ether at 0° C. was added portionwise 3.8 g (0.1 mol) of lithium aluminum hydride. The reaction mixture was stirred at room temperature for 3 h, then cooled to 0° C. and quenched by the addition of 2N aqueous sodium hydroxide solution. The mixture was dried over magnesium sulfate and filtered. The solid filter cake was washed with 50 mL of ethyl acetate. The combined organic phases were evaporated to give 7.54 g (100%) of the title compound which was used without further purification. $^1$H NMR (500 MHz, CDCl$_3$) δ 4.02 (bs, 0.7H), 3.8 (bs, 0.3H), 3.52 (d, 1.4H, J=5.9 Hz), 3.44 (d, 0.6H, J=5.9 Hz), 2.01 (m, 1.3H), 1.82 (m, 0.7H), 1.8–1.42 (m, 6H), 1.23 (m, 1H), 1.01 (m, 1H).

Step B. 4-(Triisopropylsilyloxymethyl)cyclohexanol

To a solution of 7.54 g (58 mmol) of the diol from Step A in 150 mL of dichloromethane and 20 mL of DMF at 0° C. was added 7.88 g (160 mmol) of imidazole followed by 12.3 g (13.6 mL, 63.8 mmol) of triisopropylsilyl chloride dropwise. The reaction mixture was allowed to stir overnight under nitrogen with gradual warming to room temperature. The reaction mixture was then poured into water and the organic phase was separated. The aqueous phase was washed with two portions of dichloromethane. The combined organic phases were washed sequentially with water and brine, dried over magnesium sulfate, and concentrated to give 15.8 g (95%) of the title compound which was used without further purification. $^1$H NMR (500 MHz, CDCl$_3$) δ 4.0 (bs, 0.7H), 3.96 (bs, 0.3H), 3.56 (d, 1.4H, J=5.3 Hz), 3.48 (d, 0.6H, J=5.3 Hz), 2.0 (m, 1.3H), 1.81 (m, 0.7H), 1.78–1.24 (m, 6H), 1.1 (d, 18H, J=5.5 Hz), 1.09 (m, 3H).

Step C. 4-(Triisopropylsilyloxymethyl)cyclohexanone

To a solution of 15.5 g (54 mmol) of the alcohol from Step B in dichloromethane was added 20 g of Celite and 17.5 g (81 mmol) of pyridinium chlorochromate. The reaction mixture was stirred at room temperature for a 4 h period, and then filtered. The solids were washed with dichloromethane and the combined organic phases were concentrated. The residue was purified by flash chromatography on silica gel (15% ethyl acetate/hexane) to give 13 g (85%) of the title compound. $^1$H NMR (500 MHz, CDCl$_3$) δ 3.63 (d, 2H, J=4.9 Hz), 2.49–2.32 (m, 4H), 2.12 (m, 2H), 1.96 (m, 1H), 1.49 (m, 2H) 1.07 (d, 18H, J=5.5 hz), 1.06 (m, 3H).

Step D. Methyl (4-{[(triisopropylsilyl)oxy]methyl}cyclohexylidene)acetate

To a solution of 6.37 g (35 mmol) of tri methyl phosphonoacetate in 200 mL of tetrahydrofuran (THF) was added 4.28 g (35 mmol) of potassium tert-butoxide. The reaction mixture was stirred at room temperature for 10 minutes. To the resultant slurry was added a solution of 9.3 g (32.7 mmol) of ketone from step C in 20 mL of THF. The mixture was stirred at room temperature under nitrogen overnight, then poured into water and extracted with three 100 mL portions of ether. The combined organic phases were washed sequentially with water, aqueous saturated sodium bicarbonate, and brine, dried over magnesium sulfate, and concentrated to give 10.8 g (97%) of the title compound as a clear oil which was used without further purification. $^1$H NMR (500 MHz, CDCl$_3$) δ 5.63 (s, 1H), 3.78 (m, 1H), 3.69 (s, 1H), 3.53 (m, 2H), 2.32 (m, 1H), 2.21(m, 1H), 1.97 (m, 2H), 1.76 (m, 1H), 1.10–1.03 (m 23H).

Step E. Methyl 2-[4-(triisopropylsilyloxymethyl)cyclohexyl]acetate

A mixture of 10.3 g (30.2 mmol) of the unsaturated ester from Step D and 600 mg of 5% palladium on carbon in 150 mL of methanol was stiffed under an atmosphere of hydrogen for 3 h. The catalyst was filtered off and the filtrate concentrated to give 8.8 g (85%) of the title compound as a mixture of cis and trans isomers. $^1$H NMR (500 MHz, CDCl$_3$) δ 3.68 (s, 3H), 3.57 (d, 0.6H, J=6.7 Hz), 3.39 (d, 1.4H, J=6.2 Hz), 2.32 (d, 0.6H, J=4.4 Hz), 2.21 (d, 1.4H, J=3.9 Hz), 1.82–1.60 (m, 4H), 1.54 (m, 1H), 1.45 (m, 1H), 1.1–1.05 (m, 21H), 1.01 (m, 2H).

Step F. 2-[4-(Triisopropylsilyloxymethyl)cyclohexyl]acetic acid

To a solution of 8.8 g (25.7 mmol) of methyl ester from Step E in 50 mL of THF and 50 mL of methanol was added 25 mL (24.9 mmol) of 1 N aqueous sodium hydroxide. The resultant mixture was stirred at room temperature overnight, and the solvent was removed under vacuum. The residue was diluted with ice water, and then acidified with 1 N aqueous hydrochloric acid. The mixture was extracted with three portions of ethyl acetate. The combined organics were washed with brine, dried over sodium sulfate, and concentrated to provide a quantitative yield of the title compound. $^1$H NMR (500 MHz, CDCl$_3$) δ 3.58 (d, 0.6H, J=6.7 Hz), 3.39 (d, 1.4H, J=6.2 Hz), 2.38 (d, 0.6H, J=4.4 Hz), 2.24 (d, 1.4H, J=3.9 Hz), 1.82–1.60 (m, 4H), 1.54 (m, 1H), 1.45 (m, 1H), 1.1–1.05 (m, 23H).

Step G. 4-Phenylmethyl-3-[2-[4-(triisopropylsilyloxymethyl)cyclohexyl]acetyl]-2-oxazolidinone The acid (8.5 g, 25.9 mmol) from step F was treated with 3.14 g (3.2 mL, 26 mmol) of pivaloyl chloride and 10.5 g (14.5 mL, 26 mmol) of triethylamine followed by 1.32 g (28 mmol) of lithium chloride and 4.60 g (26 mmol) of 4-phenylmethyl-2-oxazolidinone according to the procedure of G.-J. Ho and D. J. Mathre, *J. Org. Chem.* 1995, 60, 2271–2273 to provide, after purification by flash chromatography on silica gel (10% ethyl acetate/hexane), 11.5 g (91%) of the title compound. $^1$H NMR (500 MHz, CDCl$_3$) δ 7.32 (m, 2H), 7.27 (m, 1H), 7.23 (d, 2H, J=6.9 Hz), 5.31 (m, 1H), Step H. 4-Phenylmethyl-3-[2-azido-2-[4-(triisopropylsilyloxymethyl)cyclohexyl]acetyl]-2-oxazolidinone Acyl oxazolidinone (1.28 g, 2.62 mmol) from Step G in 30 mL of THF at −78° C. was treated with 5.8 mL (2.89 mmol) of a 1.5 M solution of potassium hexamethyldisilylamide in toluene followed by 973 mg (3.14 mmol) of trisyl azide in 6 mL of THF and quenched by the addition of 634 mg (10.5 mmol) of acetic acid according to the procedure of D. A. Evans et al., *J. Amer. Chem. Soc.* 1990, 10, 4011. Purification by Biotage chromatography on silica gel (25% ether/hexane) provided 720 mg (52%) of the title compound. $^1$H NMR (500 MHz, CDCl$_3$) δ 7.39–7.24 9 (m, 5H), 5.12 (d, 0.3H, J=8.7 Hz), 4.97 (d, 0.7H, J=7.5 Hz), 4.72 (m, 1H), 4.25 (m, 2H), 3.61 (d, 0.6H, J=7 Hz), 3.51 (d, 1.4H, J=5.9 Hz), 3.33 (dd, 1H, J=3 and 4 Hz), 2.87 (dt, 1H, J=3 and 10 Hz), 2.0–1.4 (m, 8H), 1.07–0.9 (m and d, 24H).

Step I. 3-[(2S)-2-azido-2-(4-{[(triisopropylsilyl)oxy]methyl}cyclohexyl)ethanoyl]-1,3-thiazolidine To a cooled (0° C.) solution of 711 mg (1.345 mmol) of 4-phenylmethyl-3-[2-azido-2-[4-(triisopropylsilyloxymethyl)cyclohexyl]acetyl]-2-oxazolidinone from Step H in 10 mL of THF/water (3:1) was added lithium hydroxide and the mixture was stirred at 0° C. for 30 min. The solution was concentrated, diluted with aqueous NaHCO$_3$ and washed with three portions of methylene chloride. The water layer was acidified to pH 1–2 with 2N hydrochloric acid and extracted with three portions of ethyl acetate. The combined organics were dried (NaSO$_4$), filtered and concentrated to give 470 mg of the alpha-azido acid. To a solution of 470 mg (1.27 mmol) of alpha-azido acid in methylene chloride (10 mL) was added 264 mg (1.38 mmol) of EDC, 186 mg (1.38 mmol) of HOBt, 0.123 mL (1.38 mmol) of thiazolidine and 0.350 mL (2.0 mmol) of diisopropylethylamine. The mixture was stirred at room temperature for 14 h and then diluted with methylene chloride. The solution was washed with saturated aqueous ammonium chloride, water and brine, dried (MgSO$_4$), filtered and concentrated. Biotage chromatography on silica gel (20% ether in hexane) of the crude mixture separated the isomers (cis and trans). Isomer I (minor component, 102 mg, less polar compound) $^1$H NMR (500 MHz, CDCl$_3$) δ 4.71–4.52 (m, 2H), 4.01–3.73 (m, 2H), 3.68 (d, 0.45H, J=7 Hz), 3.64 (d, 0.55H, J=7 Hz), 3.6 (d, 2H, 6 Hz), 3.10 (m, 1H), 3.04 (t. 1H, J=6.6 Hz), 2.21 (m, 1H), 1.78–1.24 (m, 8H), 1.09–1.01 (m and d, 23H). Isomer II (major component, 235 mg, more polar compound) $^1$H NMR (500 MHz, CDCl$_3$) δ 4.68–4.50 (m, 2H), 3.98–3.72 (m, 2H), 3.51 (d, 1H, J=6 Hz), 3.49 (d, 1H, J=6 Hz), (d, 0.45H, J=9.4 Hz), 3.64 (d, 0.55H, J=9.4 Hz), 3.11 (m, 1H), 3.04 (t. 1H, J=6.4 Hz), 2.10 (m, 1H), 1.98–1.8 (m, 3H), 1.70 (m, 1H), 1.09 (m, 1H), 1.42 (m, 1H), 1.09–1.01 (m and d, 25H).

Step J. {4-[(1S)-1-Amino-2-oxo-2-(1,3-thiazolidin-3-yl)ethyl]cyclohexyl}methanol 3-[(2S)-2-Azido-2-(4-{[(triisopropylsilyl)oxy]methyl}cyclohexyl)-ethanoyl]-1,3-thiazolidine (isomer II, 130 mg, 0.29 mmol) from Example 6, Step I was dissolved in 3 mL of 15% HF (45% in H$_2$O) in acetonitrile and stirred for 2 h. The solvent was removed and the residue was dissolved in ethyl acetate and then neutralized with aqueous sodium bicarbonate. The organics were separated, dried (Na$_2$SO$_4$) and filtered. Evaporation of the solvent afforded 78 mg of {4-[(1S)-1-azido-2-oxo-2-(1,3-thiazolidin-3-yl)ethyl]cyclohexyl}methanol. A portion of this material (24 mg, 0.084 mmol) was dissolved in wet THF and triphenyl phosphine (26 mg, 0.1 mmol) was added to the solution. The mixture was heated in an oil bath at 60° C. for 5 h, cooled, concentrated and purified by preparative TLC on silica gel (eluent: 5 to 10% methanol in CH$_2$Cl$_2$) to give the title compound. $^1$H NMR (500 MHz, CD$_3$OD, HCl salt) δ 4.71 (dd, 1H, J=3 and 6 Hz), 4.58 (d, 0.45H, J=9.2 Hz), 4.48 (d, 0.55H, J=9.2 Hz), 4.18 (d, 0.45H, J=5.9 Hz), 4.11 (d, 0.55H, J=5.9 Hz), 3.93 (m, 0.55H), 3.88 (m, 0.45H), 3.88 (m, 0.45H), 3.79 (m, 1H), 3.17 (m, 1H), 3.36 (d, 2H, J=6.1 Hz), 3.09 (m, 1H), 1.98–1.78 (m, 4H), 1.40 (m, 1H), 1.26 (m, 1H), 1.11(m, 1H), 1.01 (m, 2H). 3-[(2S)-2-Azido-2-(4-{[(triisopropylsilyl)oxy]methyl}cyclohexyl)-ethanoyl]-1,3-thiazolidine (isomer I, 78 mg) was converted to the title compound in a manner identical to that described for isomer II. $^1$H NMR (500 MHz, CD$_3$OD, HCl salt) δ 4.71 (dd, 1H, J=8 and 10 Hz), 4.58 (dd, 0.45H, J=2 and 9 Hz), 4.48 (d, 0.55H, J=2 and 9 Hz), 4.20 (d, 0.45H, J=6.2 Hz), 4.12 (d, 0.55H, J=6.2 Hz), 3.96 (m, 0.55H), 3.88 (m, 0.45H), 3.88 (m, 0.45H), 3.79 (m, 1H), 3.55 (d, 2H, J=5.9 Hz), 3.14 (m, 1H), 3.09 (m, 1H), 1.98 (m, 1H), 1.80 (m, 3H), 1.58 (m, 3H), 1.39 (m, 2H).

EXAMPLE 7

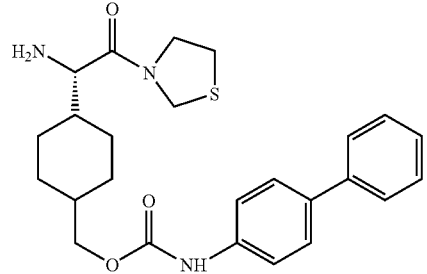

{4-[(1S)-1-Amino-2-oxo-2-(1,3-thiazolidin-3-yl)ethyl]cyclohexyl}methyl 1,1'-biphenyl-4-ylcarbamate To a solution of 27 mg (0.095 mmol) of {4-[(1S)-1-azido-2-oxo-2-(1,3-thiazolidin-3-yl)ethyl]cyclohexyl}methanol from isomer II, Example 6, Step J in 1 mL of methylene chloride was added 20 mg (0.1 mmol) of 4-biphenylisocyanate and 0.02 mL of triethylamine. The mixture was stirred for 6 h and directly subjected to preparative TLC (silica gel, 45% ethyl acetate in hexane) to give the carbamate. The carbamate was dissolved in wet THF and to this solution was added 25 mg (excess) of triphenyl phosphine. The reaction mixture was heated at 60° C. for 3 h. Purification by preparative TLC on silica gel (eluent: 10% MeOH in CH$_2$Cl$_2$) gave the title compound. $^1$H NMR (500 MHz, CD$_3$OD, HCl salt) δ 7.56–7.48 (m, 6H), 7.40 (t, 2H, J=7.5 Hz), 7.28 (t, 1H, J=6.0 Hz), 4.72 (m, 1H), 4.59 (d, 0.45H, J=9.2 Hz), 4.49 (d, 0.55H, J=9.2 Hz), 4.19 (d, 0.45H, J=5.9 Hz), 4.11 (d, 0.55H, J=5.9 Hz), 3.99 (d, 2H, J=6.3 Hz), 3.93 (m, 0.55H), 3.88 (m, 0.45H ), 3.76 (m, 1H), 3.2–3.05 (m, 2H), 1.98–1.80 (m, 5H), 1.71 (m, 1H), 1.27–1.09 (m, 4H).

Essentially following the procedures outlined for Examples 1–7 the compounds listed in Tables 1–4 were prepared TABLE 1
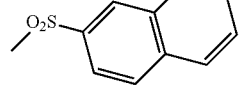
| Example | X | R | ¹H NMR data |
|---|---|---|---|
| 8 | S | MeSO₂— | 2.93 (s, 3H) |
| 9 | S | 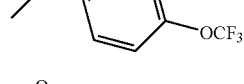 | 8.41 (s, 1H), 8.05–8.01 (m, 2H), 7.97 (dd, 1H, J=8,1Hz), 7.84 (dd, 1H, J=8,1Hz), 7.69–7.61 (m, 2H) |
| 10 | S | 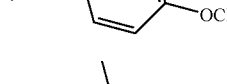 | 7.97 (d, 2H, J=8Hz), 7.43 (d, 2H, J=8Hz) |
| 11 | CH₂ | 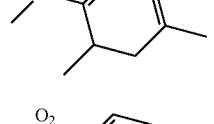 | 7.97 (d, 2H, J=8Hz), 7.43 (d, 2H, J=8Hz), 3.59–3.53 (m, 1H), 3.47–3.30 (4H), 1.98–1.73 (m, 7H) |
| 12 | S | 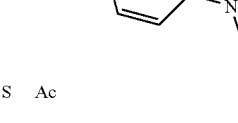 | 6.99 (s, 2H), 2.59 (s, 6H), 2.27 (s, 3H) |
| 13 | CH₂ | 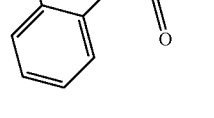 | 7.81–7.72 (m,4H), 3.96–3.87 (m, 3H), 3.59–3.54 (m, 3H), 3.33–3.28 (m, 2H), 1.69–1.58 (m, 3H), 1.38–1.25 (m, 10H), 0.92–0.86 (m, 3H) |
| 14 | S | Ac | 1.91 (s, 3H) |
| 15 | S | 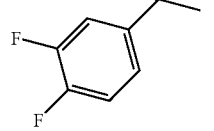 | 7.32–7.23 (m, 2H), 7.14–7.02 (m, 2H), 3.52 (s, 2H) |
| 16 | S | 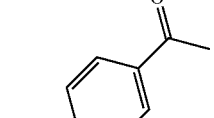 | 7.78–7.71 (m, 1H), 7.68–7.62 (m, 1H), 7.37–7.32 (m, 1H) |
| 17 | S |  | 7.91 (d, 2H, J=8z), 7.35 (d, 2H, J=8Hz) |

TABLE 1-continued
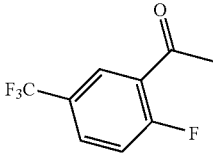
| Example | X | R | ¹H NMR data |
|---|---|---|---|
| 18 | S | 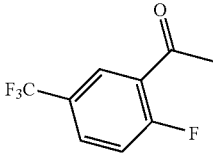 | 7.93 (s, 1H), 7.84 (s, 1H), 7.41 (t, 1H, J=9.4Hz) |
| 19 | S |  | 7.78 (t, 1H, J=7.3Hz), 7.60–7.53 (m, 2H) |
| 20 | S |  | 8.00–7.92 (m, 2H), 7.79 (s, 1H) |
| 21 | S | 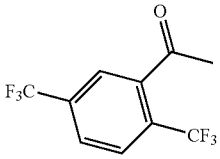 | 8.18–8.10 (m, 2H), 7.43 (t, 1H, J=9.5Hz) |
| 22 | S | 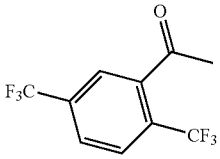 | 7.74 (d, 1H, J=7.8Hz), 7.70–7.59 (m, 2H), 7.48 (d, 1H, J=7.3Hz) |
| 23 | S | 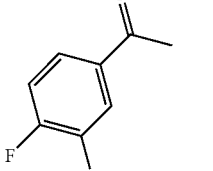 | 7.57–7.51 (m, 2H), 7.46–7.42 (m, 1H) |

TABLE 1-continued
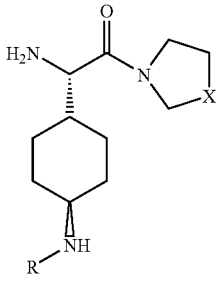
| Example | X | R | $^1$H NMR data |
|---|---|---|---|
| 24 | S | 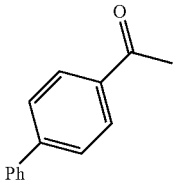 | 7.88 (d, 2H, J=8.5Hz), 7.70 (d, 2H, J=8.4Hz), 7.65 (d, 2H, 7.5Hz), 7.46 (t, 2H, J=7.6Hz), 7.37 (t, 1H, J=7.2Hz) |
| 25 | S | 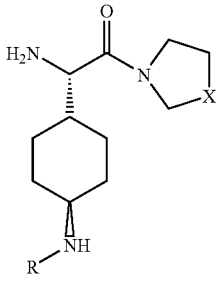 | 7.62 (d, 1H, J=6.8Hz), 7.54 (dd, 1H, J=2.1, 9.4Hz), 7.51–7.43 (m, 1H), 7.27 (td, 1H, J=8.4, 2.6Hz) |
| 26 | S | 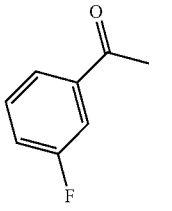 | 7.38–7.34 (m, 1H), 7.29–7.19 (m, 2H) |
| 27 | S | 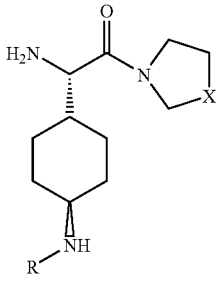 | 8.35 (s, 1H), 7.96–7.85 (m, 4H), 7.57 (quin, 2H, J=6Hz) |
| 28 | S | 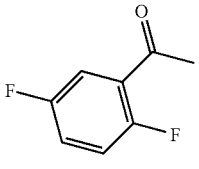 | 8.14 (d, 1H, J=8Hz), 7.96 (d, 1H, J=7.2Hz), 7.91 (dd, 1H, J=2.5,6Hz), 7.58–7.47 (m, 4H) |
| 29 | S | 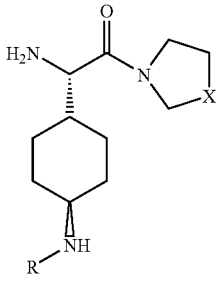 | 7.46–7.42 (m, 2H), 6.99 (d, 1H, J=8.2Hz), 3.87 (s, 6H) |

TABLE 1-continued
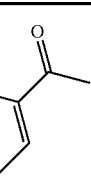
| Example | X | R | ¹H NMR data |
|---------|---|---|-------------|
| 30 | S | 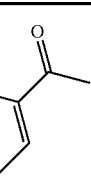 | 7.73 (d, 2H, J=8.3Hz), 7.48 (d, 2H, J=8.3Hz), 1.33 (s, 9H) |
| 31 | S | 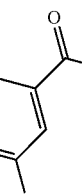 | 8.42 (s, 2H), 8.17 (s, 1H), |
| 32 | S | 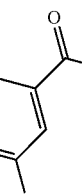 | 7.43–7.36 (m, 3H)7.53–7.46 (m, 2H), 7.25 (d, 1H, J= |
| 33 | S | 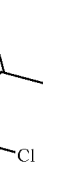 | 7.97 (d, 1H, J=1.8Hz), 7.72 (dd, 1H, J=2,8.2Hz), 7.61 (d, 1H, J=8.2Hz) |
| 34 | S | 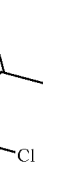 | 7.53 (s, 1H), 7.39 (s, 2H) |
| 35 | S | 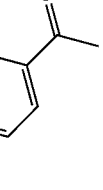 | 7.69 (d, 2H, J=8Hz), 7.25 (d, 2H, J=8Hz), 2.38 (s, 3H) |

TABLE 1-continued
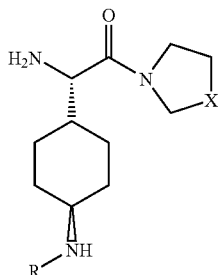
| Example | X | R | ¹H NMR data |
|---|---|---|---|
| 36 | S | 4-fluorophenyl ketone | 7.87–7.83 (m, 2H), 7.18 (t, 2H, J= 10Hz) |
| 37 | S | 1H-indol-2-yl ketone | 7.58 (d, 1H, J=8Hz), 7.42 (d, 1H, J=8.2Hz), 7.20 (t, 1H, J=7.6Hz), &.08 (s, 1H), 7.05 (t, 1H, J=7.6Hz) |
| 38 | S | 1H-indol-3-yl ketone | 8.07 (d, 1H, J=7.8Hz), 7.87 (s, 1H), 7.41 (d, 1H, J=8Hz), 7.20–7.11 (m, 2H) |
| 39 | S | 2-(pyridin-3-yl)thiazol-4-yl ketone | 9.29 (s, 1H), 8.69 (d, 1H, J=4.8Hz), 8.53 (d, 1H, J=8Hz), 8.31 (s, 1H), 7.65 (dd, 1H, J=4.8, 8Hz) |
| 40 | S | pyridin-2-yl ketone | 8.63 (s, 1H), 8.20–7.96 (m, 2H), 7.62–7.58 (m, 1H) |
| 41 | S | 2-benzylphenyl ketone | 7.38–7.18 (m, 7H), 7.15–7.12 (m, 2H), 4.14 (s, 2H) |
| 42 | S | pyridin-3-yl ketone | 9.04 (s, 1H), 8.77 (d, 1H, J=5Hz), 8.45 (d, 1H, J=8.2Hz), 7.73 (dd, 1H, J= 8, 5.2Hz) |

TABLE 1-continued
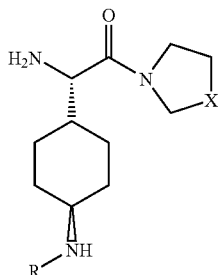
| Example | X | R | ¹H NMR data |
|---|---|---|---|
| 43 | S | 4-acetylpyridine | 8.84 (bs, 2H), 8.08 (d, 2H, J=5.8Hz) |
| 44 | S | 2-acetylfuran | 7.64 (s, 1H), 7.09 (d, 1H, J=3.4Hz), 6.57 (d, 1H, J=3.4Hz) |
| 45 | S | 4-(dimethylamino)acetophenone | 7.73 (d, 2H, J=10Hz), 6.79 (d, 2H, J=10Hz), 3.02 (s, 6H) |
| 46 | S | 5-acetylisoxazole | 8.51 (s, 1H), 6.95 (s, 1H) |
| 47 | S | 4-(trifluoromethoxy)phenylacetone | 7.37 (d, 2H, J=8z), 7.19 (d, 2H, J=8Hz), 7.46 (s, 2H) |
| 48 | S | 4-[3-(trifluoromethoxy)phenyl]-2-butanone | 7.36 (t, 1H, J=8Hz), 7.19 (dd, 1H, J=1,8Hz), 7.12–7.05 (m, 2H), 2.94 (t, 2H, J=7Hz), 2.43 (t, 2H, J=7Hz) |
| 49 | S | benzyl acetate | 7.37–7.26 (m, 5H), 5.04 (s, 2H) |

TABLE 1-continued
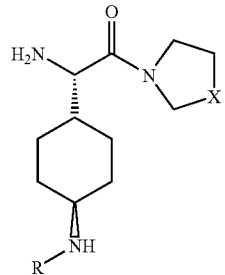
| Example | X | R | ¹H NMR data |
|---|---|---|---|
| 50 | CH₂ | 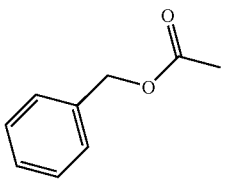 | 7.37–7.26 (m, 5H), 5.04 (s, 2H), 3.63–3.57 (m, 1H), 3.52–3.30 (5H), 2.01–1.85 (m, 7H) |
| 51 | S | 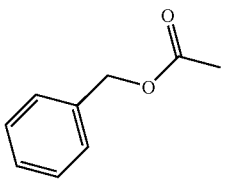 | 7.25–7.18 (m, 4H), 5.01 (s, 2H), 2.87 (sept, 1H, J=6Hz), 1.21 (d, 6H, J=6Hz) |
| 52 | S | 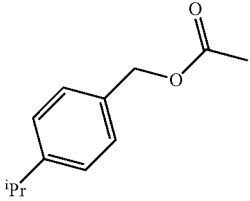 | 7.52–7.47 (m, 2H), 7.24 (d, 1H, J=8Hz), 5.02 (s, 2H) |
| 53 | CH₂ | 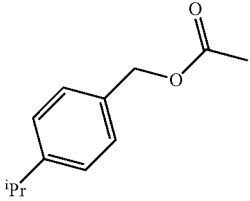 | 7.53–7.46 (m, 2H), 7.25 (d, 1H, J=8Hz), 5.02 (s, 2H) |
| 54 | S | 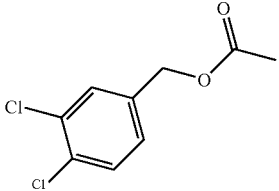 | 8.04 (d, 1H, J=10Hz), 7.84 (d, 1H, J=10Hz), 7.81 (d, 1H, J=10Hz), 7.56–7.40 (m, 4H), 5.54 (s, 2H) |

TABLE 1-continued
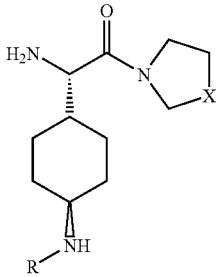
| Example | X | R | ¹H NMR data |
|---|---|---|---|
| 55 | CH₂ | 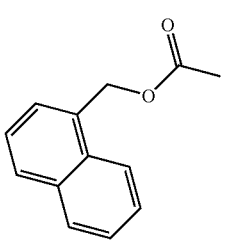 | 8.04 (d, 1H, J=8Hz, 7.91–7.82 (m, 2H), 7.57–7.41 (m, 4H), 5.53 (s, 2H) |
| 56 | S | 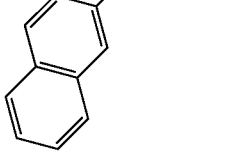 | 7.84–7.79 (m, 4H), 4.47–7.43 (m, 3H), 5.21 (s, 2H) |
| 57 | S | 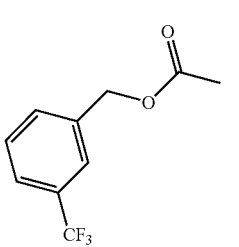 | 7.64 (s, 1H), 7.62–7.52 (m, 3H), 5.15 (s, 2H) |
| 58 | CH₂ | 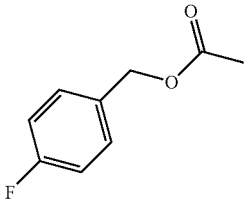 | 7.63 (s, 1H), 7.61–7.53 (m, 3H) |
| 59 | S |  | 7.38–7.35 (m, 2H), 7.07–7.03 (m, 2H), 5.02 (s, 2H) |

TABLE 1-continued
| Example | X | R | ¹H NMR data |
|---|---|---|---|
| 60 | S | 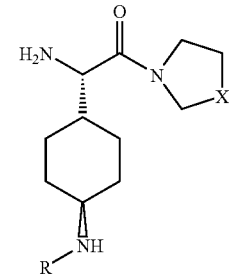 | 8.37 (s, 1H), 6.41 (s, 1H), 5.18 (s, 2H) |
| 61 | S | 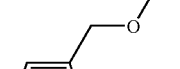 | 3.17–3.06 (m, 4H), 1.07 (t, 3H, J=7Hz) |
| 62 | S |  | 7.41 (d, 2H, J=8z), 7.15 (d, 2H, J=8Hz) |
| 63 | S |  | 7.72 (d, 1H, J=7.5Hz), 7.45–7.41 (m, 2H), 7.38–7.29 (m, 4H), 7.22 (d, 1H, J=6Hz), 7.17–7.14 (m, 1H) |
| 64 | S | 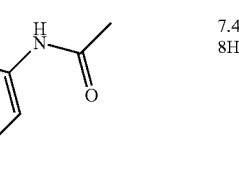 | 7.35–7.27 (m, 4H), 7.04 (t, 1H, J=6Hz), 6.93–6.87 (m, 4H) |
| 65 | S | 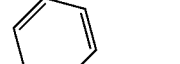 | 7.56 (d, 2H, J=7.5Hz), 7.53 (d, 2H, J=7.5Hz), 7.43–7.37 (m, 4H), 7.26 (t, 1H, J=7Hz) |
| 66 | S | 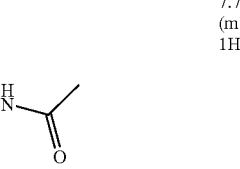 | 7.34 (dt, 1H, J=12,1), 7.19 (q, 1H, J=7Hz), 6.98 (dd, 1H, J = 7,1Hz), 6.65 (td, 1H, J=7,1Hz) |

TABLE 1-continued
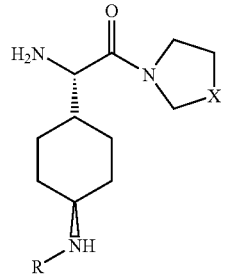
| Example | X | R | ¹H NMR data |
|---|---|---|---|
| 67 | S | 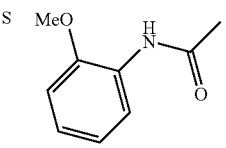 | 7.94 (d, 1H, J=9Hz), 6.95–6.83 (m, 3H) |
| 68 | S | 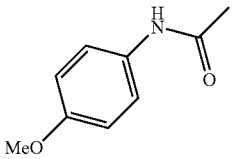 | 7.23 (d, 2H, J= 10Hz), 6.83 (d, 2H, J=10Hz) |
| 69 | S | 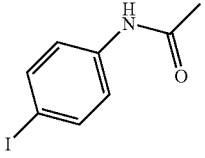 | 7.55 (d, 2H, J=10Hz), 7.18 (d, 2H, J=10Hz) |
| 70 | S | 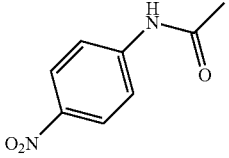 | 8.14 (d, 2H, J=9Hz), 7.38 (d, 2H, J=9Hz) |
| 71 | S | 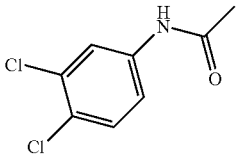 | 7.73 (d, 1H, J=1Hz), 7.36 (d, 1H, J=8Hz), 7.19 (dd, 1H, J= 1,8Hz) |
| 72 | S | 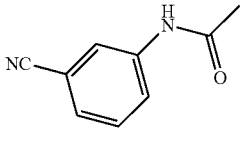 | 7.83 (s, 1H), 7.53 (d, 1H, J= 8.5Hz), 7.39 (t, 1H, J=8Hz), 7.26 (d, 1H, J=7.5Hz) |
| 73 | S | 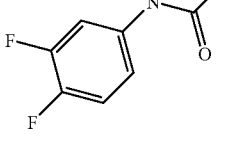 | 7.51–7.42 (m, 1H), 7.09 (q, 1H, J= 12Hz), 6.95–6.92 (m, 1H) |

TABLE 1-continued
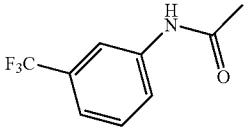
| Example | X | R | ¹H NMR data |
|---|---|---|---|
| 74 | S | 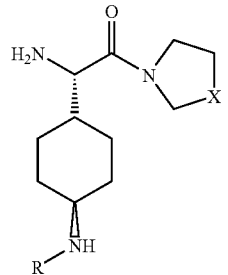 | 7.80 (s, 1H), 7.48 (d, 1H, J= 7.5 Hz), 7.39 (t, 1H, J= 7.5Hz), 7.21 (d, 1H, J=7.5Hz) |
TABLE 2
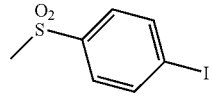
| Example | R | ¹H NMR data |
|---|---|---|
| 75 | 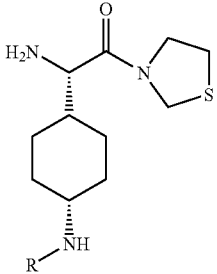 | 7.95 (d, 2H, J=8Hz), 7.61 (d, 2H, J=8Hz) |
| 76 | 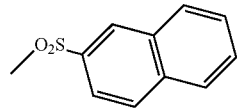 | 8.42 (s, 1H), 8.05–8.01 (m, 2H), 7.97 (dd, 1H, J=8,1Hz), 7.86 (dd, 1H, J=8,1Hz), 7.69–7.61 (m, 2H) |
| 77 | 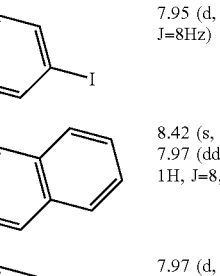 | 7.97 (d, 2H, J=8Hz), 7.46 (d, 2H, J=8Hz |
| 78 | 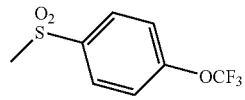 | 7.42–7.36 (m, 2H), 7.27–7.22 (m, 1H) |
| 79 | 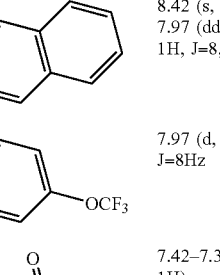 | 7.38–7.25 (m, 5H), 5.05 (s, 2H) |

TABLE 3
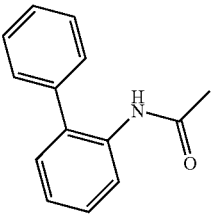
| Example | X | R | ¹HNMR data |
|---|---|---|---|
| 80 | S | 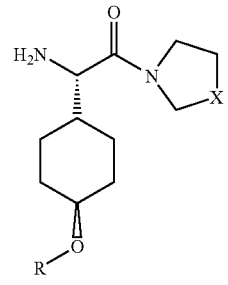 | 7.58 (bd, 1H), 7.42–7.39 (m, 2H), 7.37–7.29 (m, 4H), 7.28–7.20 (m, 2H |
| 81 | S | 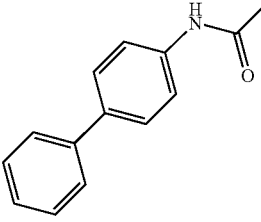 | 7.59–7.46 (m, 6H), 7.39 (t, 2H, J=7Hz), 7.27 (t, 1H, J=7Hz) |
| 82 | S | 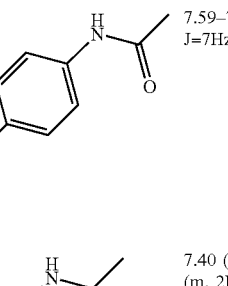 | 7.40 (d, 2H, J=8.5Hz), 7.33–7.28 (m, 2H), 7.05 (t, 1H, J=8Hz), 6.95–6.89 (m, 4H) |
| 83 | S | 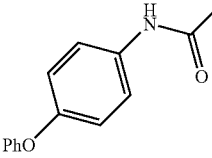 | 7.35 (d, 1H, J=12), 7.21 (q, 1H, J=7Hz), 7.09 (dd, 1H, J=7,1Hz), 6.70 (td, 1H, J=7,1.5Hz) |
| 84 | S | 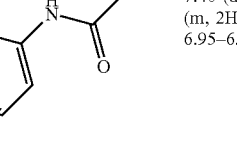 | 7.29 (d, 2H, J=8Hz), 6.82 (d, 2H, J=8Hz) |
| 85 | S | 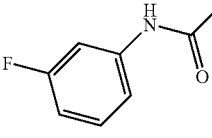 | 7.58 (d, 2H, J=8Hz), 7.23 (d, 2H, J=8Hz) |
| 86 | S | 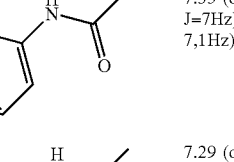 | 8.18 (d, 2H, J=9Hz), 7.63 (d, 2H, J=9Hz) |

TABLE 3-continued
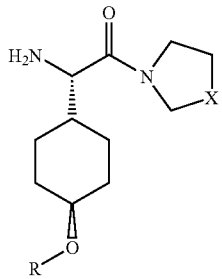
| Example | X | R | ¹HNMR data |
|---|---|---|---|
| 87 | S | 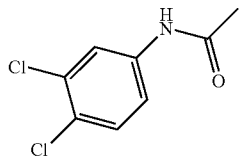 | 7.72 (d, 1H, J=2Hz), 7.38 (d, 1H, J=8Hz), 7.29 (dd, 1H, J=8,2Hz) |
TABLE 4
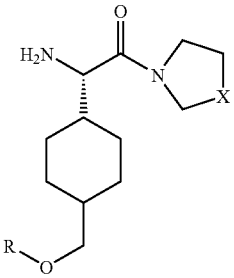
| Example | Isomer | X | R | ¹H NMR data |
|---|---|---|---|---|
| 88 | I | S | 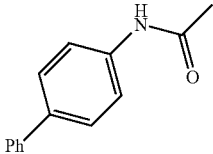 | (500 MHz, CD$_3$OD HCl salt) 7.60–7.43 (m, 6H), 7.40 (t, 2H, J=7.7 Hz), 7.28 (t, 1H, J=7.4 Hz) |
| 89 | I | S | 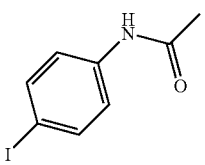 | (500 MHz, CD$_3$OD, HCl salt) 7.57 (d, 2H, J=8.7 Hz), 7.24 (d, 2H, J=8.7 Hz) |
| 90 | II | S | 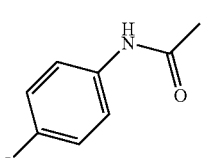 | (500 MHz, CD$_3$OD, HCl salt) 7.57 (d, 2H, J=8.7 Hz), 7.24 (d, 2H, J=8.7 Hz) |
| 91 | II | S | 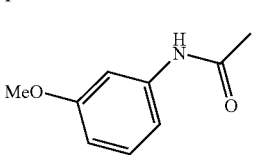 | (500 MHz, CD$_3$OD, HCl salt) 7.14 (t, 1H, J=4.6 Hz), 7.13 (bs, 1H), 6.92 (d, 1H, J=8 Hz), 6.59 (d, 1H, J=2 and 8 Hz) |

TABLE 4-continued

[Structure: H2N-CH(-C(=O)-N-pyrrolidine-X)-cyclohexyl-CH2-O-R]

| Example | Isomer | X | R | ¹H NMR data |
|---------|--------|---|---|-------------|
| 92 | II | S | [4-fluorobenzyl -C(=O)- group] | (500 MHz, CD₃OD, HCl salt) 7.40 (m, 2H), 7.01 (m, 2H) |
| 93 | II | S | [4-methoxyphenyl-NH-C(=O)- group] | (500 MHz, CD₃OD, HCl salt) 7.28 (dd, 2H, J=2 and 7Hz), 6.64 (t, 2H, J=10.3 Hz), 3.76 (s, 1.35H), 3.75 (s, 1.65H) |

EXAMPLE 94

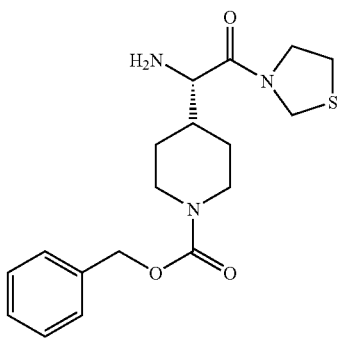

Step A. Methyl[(tert-butoxycarbonyl)amino](piperidin-4-yl)acetate

To a solution of 2.51 g (10.76 mmol) of 1-(benzyloxycarbonyl)-4-piperidone and 3.03 g (10.2 mmol) of Boc-α-phosphonoglycine trimethyl ester in 20 mL of methylene chloride was added 1.98 g (13 mmol) of 1,8-diazabicyclo[5.4.0]-undec-7-ene (DBU) dropwise at room temperature under nitrogen. The reaction mixture was stirred at room temperature for 3 days and then poured into water and extracted with methylene chloride (30 mL×3). The combined organics were washed sequentially with water and brine, dried over anhydrous MgSO₄ and filtered. Evaporation of the solvent was followed by flash chromatography (silica gel, eluent: 40% ethyl acetate in hexanes) to give 3.1 g of the adduct. The adduct was dissolved in methanol (30 mL) and to this solution was added 300 mg of palladium hydroxide on activated carbon (~20% Pd). The reaction was shaken under an atmosphere of hydrogen (40 psi) for 3 h, filtered through a pad of Celite and concentrated to give the title compound. ¹H NMR (500 MHz, CDCl₃) δ 4.09 (d, 1H, J=6 Hz), 3.71 (s, 3H), 3.2 (bd, 2H, J=12 Hz), 2.59 (dd, 2H, J=12 and 8 Hz), 1.9 (m, 1H), 1.6 (m, 2H), 1.4 (s, 9H), 1.31 (m, 2H).

Step B. [(tert-Butoxycarbonyl)amino][1-(3-phenylpropanoyl)piperidin-4-yl]acetic acid To a solution of 715 mg (2.625 mmol) of methyl [(tert-butoxycarbonyl)amino](piperidin-4-yl)acetate from Step A in 10 mL of methylene chloride was added 303 mg (0.418 mL, 3.0 mmol) of triethylamine followed by 492 mg (2.88 mmol) of benzyl chloroformate and the reaction mixture was stirred at room temperature for 8 h. The reaction mixture was diluted with methylene chloride (30 mL), washed sequentially with 2N hydrochloric acid, saturated aqueous sodium bicarbonate, and brine. The solution was dried (anhydrous MgSO₄), filtered and concentrated. Evaporation of solvent followed by flash chromatography (silica gel, eluent: 30% ethyl acetate in hexane) gave the benzyl carbamate. To a cooled (ice/water bath) solution of 324 mg (0.798 mmol) of benzyl carbamate in methyl alcohol (10 mL) was added 2N aqueous NaOH (4 mL, excess) and the mixture was stirred at room temperature for 4 h. The reaction mixture was concentrated, partitioned between ethyl acetate and water, and then carefully acidified with 2N hydrochloric acid (final pH=4). The organics were separated, and the water layer was extracted with ethyl acetate (×2). The combined organics were dried (anhydrous Na₂SO₄) and filtered. Evaporation of solvent gave the title compound which was used without further purification. ¹H NMR (500 MHz, CDCl₃) δ

7.41–7.24 (m, 5H), 5.21 (d, 1H, J=6 Hz), 5.1 (s, 2H), 4.2 (bs, 2H), 3.7 (bs, 2H), 1.96 (bs, 1H), 1.7–1.5 (m, 2H), 1.4 (s, 9H), 1.3 (m, 2H).

Step C. Benzyl 4-[(1S)-1-amino-2-oxo-2-(1,3-thiazolidin-3-yl)ethyl]piperidine-1-carboxylate To a solution of 100 mg (0.255 mmol) of [(tert-butoxycarbonyl)-amino][1-(3-phenylpropanoyl)piperidin-4-yl]acetic acid from Step B in methylene chloride (5 mL) was added 53 mg (0.27 mmol) of EDC, 37 mg (0.27 mmol) of HOBt, 0.043 mL (0.27 mmol) of thiazolidine and 0.042 mL (0.3 mmol) of triethylamine. The mixture was stirred at room temperature for 4 h and then diluted with methylene chloride. The solution was washed sequentially with saturated aqueous ammonium chloride, water and brine, dried (MgSO$_4$) and then filtered. Evaporation of the solvent followed by flash chromatography (silica gel, eluent: 40% ethyl acetate in hexane) gave 102 mg of the title compound as its BOC protected derivative. The individual enantiomers were separated by HPLC (ChiralCel OJ column, eluent: 15% ethanol in hexane) and then the BOC group was removed by treatment with freshly prepared HCl/MeOH (10 mL) for 3 h and then concentrated to give the title compound in, enantiomerically pure form as its HCl salt. $^1$H NMR (less polar compound, 500 MHz, CD$_3$OD, HCl salt) δ 7.36 (s, 4H), 7.31 (m, 1H), 5.1 (s, 2H), 4.51–4.42 (m, 2H), 4.22–4.18 (m, 2H), 3.92 (m, 1H), 3.79 (m, 1H), 3.18–3.08 (m, 2H), 2.81 (bs, 2H), 2.11 (m, 1H), 1.71 (m, 1H), 1.42–1.28 (m, 2H).

EXAMPLE 95

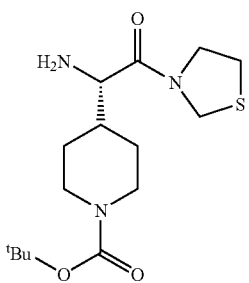

Step A. [1-(tert-Butoxycarbonyl)piperidin-4-yl]acetic acid

To a cooled (0° C.) solution of 10.87 g (60 mmol) of trimethyl phosphonoacetate in dry tetrahydrofuran (THF, 150 mL) was added 6.96 g (62 mmol) of potassium t-butoxide in portions. After stirring the mixture at room temperature for 10 min, a solution of 11.16 g (56 mmol) of 1-Boc-4-piperidone in THF (30 mL) was added dropwise. The mixture was stirred at room temperature for 12 h, concentrated and partitioned between water and ether. The ether layer was separated and the water layer was extracted with ethyl acetate (×2). The combined organics were washed (water, brine), dried (MgSO$_4$) and filtered. Evaporation of the solvent gave 13.6 g of the α,β-unsaturated ester. The ester was dissolved in methanol (200 mL) and 680 mg of palladium hydroxide was added and then hydrogen was introduced by a balloon for 5 h. The catalyst was removed by filtration through a pad of Celite and the filtrate was concentrated to give the saturated ester. The crude ester was dissolved in methanol (100 mL) and 4N aqueous NaOH (20 mL, excess) was added to the solution. The mixture was stirred for 8 h, concentrated and the acidified with 1N hydrochloric acid at 0° C. The organics were extracted with ethyl acetate (×3), washed with brine, dried over Na$_2$SO$_4$, filtered and then concentrated to give the acid (12 g). $^1$H NMR (500 MHz, CDCl$_3$) δ 4.1 (bs, 2H), 2.74 (bs, 2H), 2.31 (d, 2H, J=6.9 Hz), 1.95 (m, 1H), 1.74 (bd, 2H, J=12.6 Hz), 1.46 (s, 9H), 1.19 (dd, 2H, J=6 and 3.5 Hz)

Step B. tert-Butyl 4-[(1S)-1-amino-2-oxo-2-(1,3-thiazolidin-3-yl)ethyl]piperidine-1-carboxylate Acid (Example 95, step A. 4.01 g) was converted to tert-butyl 4-[(1S)-1-azido-2-oxo-2-(1,3-thiazolidin-3-yl)ethyl]piperidine-1-carboxylate (1.3 g) in 4 steps using the procedures outlined in Example 6. $^1$H NMR (500 MHz, CD$_3$OD, HCl salt) δ 4.71–4.49 (m, 2H), 4.09 (bs, 2H), 3.98–3.74 (m, 2H), 3.42 (d, 0.4H, J=7 Hz), 3.40 (d, 0.6H, J=7 Hz), 3.18 (t, 1.2H, J=5.6 Hz), 3.02 (t, 0.8H, J=5.6 Hz), 2.72 (bs, 2H), 2.18 (m, 1H), 1.99 (d, 1H, J=13 Hz), 1.61 (d, 1H, J=13.5 Hz), 1.42 (s, 9H), 1.24 (m, 1H), 1.19 (m, 1H). A portion of this material (30 mg) was dissolved in wet THF and triphenyl phosphine (26 mg) was added to the solution. The mixture was heated at 60° C. for 5 h, cooled, concentrated and purified by preparative TLC on silica gel (eluent: 5 to 10% methanol in CH$_2$Cl$_2$) to give the title compound. $^1$H NMR (500 MHz, CDCl$_3$) δ 4.68–4.48 (m, 2H), 4.18 (bs, 2H), 3.99–3.69 (m, 2H), 3.36 (d, 0.4H, J=7 Hz), 3.29 (d, 0.6H, J=7 Hz). 3.1 (t, 1.2H, J=5.6 Hz), 3.0 (t, 0.8H, J=5.6 Hz), 2.61 (bs, 2H), 1.92 (bd, 1H, J=13.5 Hz), 1.65 (m, 1H), 1.58 (m, 1H), 1.42 (s, 9H), 1.25 (m, 1H), 1.20 (m, 1H).

EXAMPLE 96

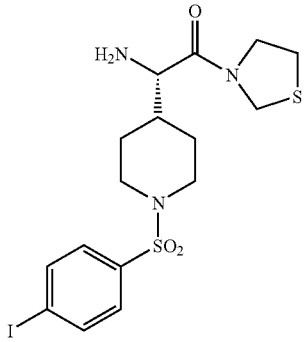

Step A. Benzyl (1S)-2-oxo-1-piperidin-4-yl-2-(1,3-thiazolidin-3-yl)ethylcarbamate To a solution of 789 mg (2.35 mmol) of tert-butyl 4-[(1S)-1-azido-2-oxo-2-(1,3-thiazolidin-3-yl)ethyl]piperidine-1-carboxylate in Example 95, Step B in wet THF (10% water, 20 mL) was added 602 mg (2.4 mmol) of triphenyl phosphine and the mixture was heated in an oil bath at 60° C. for 5 h. The reaction mixture was cooled, concentrated and purified by flash column (silica gel, eluent: 5 to 10% methanol in CH$_2$Cl$_2$) to give 770 mg of the amine. To a solution of 770 mg (2.12 mmol) of amine in methylene chloride (10 mL) was added 0.557 mL (4 mmol) of triethylamine and 0.335 mL (2.35 mmol) benzyl chloroformate and the mixture was stirred at room temperature for 3 h and concentrated. Purification by flash chromatography (silica gel, eluent: 60% ethyl acetate in hexane) gave 680 mg of the Cbz compound. The Cbz compound (680 mg, 1.47 mmol) was dissolved in freshly prepared HCl/MeOH (10 mL) and stirred for 3 h and then concentrated to give the title compound as its HCl salt. $^1$H NMR (500 MHz, CD3OD) δ

7.38 (m, 5H), 5.09 (s, 1H), 4.8–4.46 (m 2H), 4.39 (m, 1H), 4.0–3.78 (m, 2H), 3.39 (bt, 2H), 3.12–3.01 (m, 2H), 2.97 (bt, 2H), 2.1 (m, 1H), 2.0 (bd, 1H), 1.82 (bd, 1H), 1.54 (m, 2H).

Step B. (1S)-1-{1-[(4-Iodophenyl)sulfonyl]piperidin-4-yl}-2-oxo-2-(1,3-thiazolidin-3-yl)ethanamine To a solution of 40 mg (0.1 mmol) of amine hydrochloride from step A in methylene chloride (1 mL) was added 0.035 mL (0.25 mmol) of triethylamine and 29.4 mg (0.12 mmol) of 4-iodophenylsulfonyl chloride. The mixture was stirred for 3 h and the mixture was subjected directly to preparative TLC on silica gel (eluent: 5% CH$_3$OH in CH$_2$Cl$_2$) to give 38.8 mg of the desired sulfonamide as an off white solid. This material was cooled to 0° C. and 30% HBr/AcOH (0.5 mL) was added. After stirring for 2 h, the reaction mixture was triturated with ether (×3) and the solid was collected and washed with ether and dried to give the title compound as its HBr salt. $^1$H NMR (500 MHz, CD3OD) δ 7.67 (d, 2H, 8.4 Hz), 7.47 (d, 2H, J=8.4 Hz), 4.66–4.43 (m, 2H), 3.87–3.7 (m, 3H), 3.11–2.99 (m, 2H), 2.21 (bt, 2H), 1.87 (bd, 1H), 1.61 (m, 1H), 1.44 (m, 2H), 1.35 (m, 1H).

EXAMPLE 97

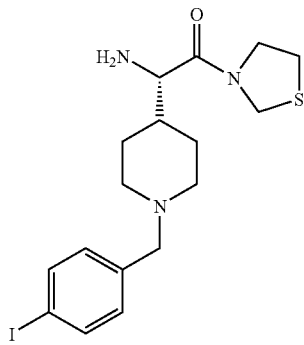

(1S)-1-[1-(4-Iodobenzyl)piperidin-4-yl]-2-oxo-2-(1,3-thiazolidin-3-yl)ethanamine tert-Butyl 4-[(1S)-1-azido-2-oxo-2-(1,3-thiazolidin-3-yl)ethyl]piperidine-1-carboxylate (Example 96, step B, 215 mg, 0.6 mmol) was dissolved in a freshly prepared HCl in methanol (1 mL acetyl chloride in 9 mL of methanol) and stirred for 4 h and concentrated to remove the Boc group. A portion of this material (29 mg, 0.1 mmol) was dissolved in methylene chloride (1 mL) and triethylamine (0.041 mL, 0.3 mmol) and 4-iodobenzylbromide (44 mg, 0.15 mmol) was added. The reaction mixture was stirred for 8 h, concentrated and purified by flash chromatography (silica gel, eluent: 20% acetone in CH$_2$Cl$_2$) to give the 4-iodobenzylamine. This material was dissolved in wet THF (10% water) and triphenyl phosphine (26 mg, 0.1 mmol) was added. The reaction mixture was heated in an oil bath at 60° C. for 3 h, concentrated and subjected to preparative TLC on silica gel (eluent: 10% MeOH in CH2Cl2) to afford 32 mg of the title compound. $^1$H NMR (500 MHz, CD3OD) δ 7.85 (d, 2H, J=6 Hz), 7.34 (d, 2H, J=6 Hz), 4.75–4.46 (m, 2H), 4.38–4.28 (m, 1H), 4.47 (s, 2H), 3.92–3.64 (m, 2H), 4.53 (bs, 2H), 3.16–3.02 (m, 4H), 2.19 (m, 1H), 1.98 (m, 2H), 1.83 (m, 2H).

Essentially following the procedures outlined for Examples 94–97 the compounds listed in Tables 5 and 6 were prepared

TABLE 5

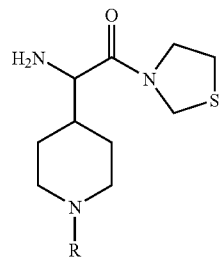

| Example | R | $^1$HNMR data |
|---------|---|---------------|
| 98 |  | (500 MHz, CD$_3$OD, HCl salt) 8.38 (s, 1H), 8.07 (m, 2H), 8.0 (d, 1H, J=10 Hz), 7.79 (d, 1H, J=10 Hz), 7.7 (m, 2H) |

TABLE 5-continued
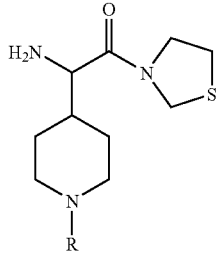
| Example | R | ¹HNMR data |
|---|---|---|
| 99 | 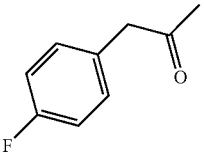 | (500 MHz, CD₃OD, HCl salt) 7.22 (m, 2H), 7.02 (m, 2H), 3.74 (m, 2H, C$\underline{H}_2$-Ph-F) |
| 100 | 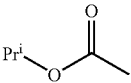 | (500 MHz, CD₃OD, HCl salt) 1.22 (d, 6H, J=7Hz) |
| 101 | 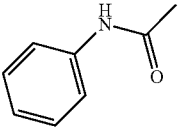 | (500 MHz, CD₃OD, HCl salt) 7.31 (m, 2H), 7.23 (m, 2H), 7.01 (m, 1H) |
TABLE 6
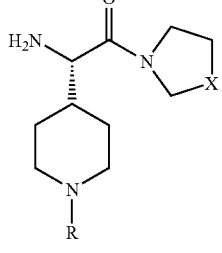
| Example | X | R | ¹H NMR data |
|---|---|---|---|
| 102 | S | 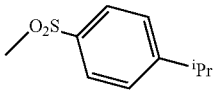 | (500 MHz, CD₃OD, HBr salt) 7.69 (d, 2H, J=8Hz), 7.48 (d, 2H, J=8 Hz), 1.25 (d, 6H, J=7Hz) |
| 103 | S | 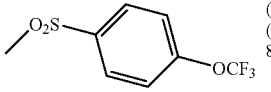 | (500 MHz, CD₃OD, HBr salt) 7.89 (d, 2H, J=8.7 Hz), 7.52 (d, 2H, J=8.7Hz) |
| 104 | S | 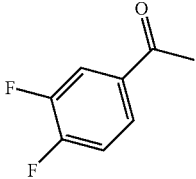 | (500 MHz, CD₃OD, HBr salt) 7.38 (m, 2H), 7.22 (m, 1H) |

TABLE 6-continued
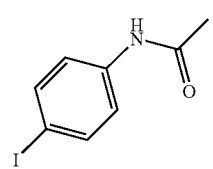
| Example | X | R | ¹H NMR data |
|---|---|---|---|
| 105 | S | 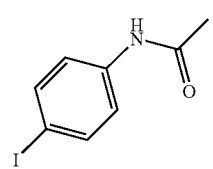 | (500 MHz, CD₃OD) 7.54 (d, 2H, J=9Hz), 7.16 (d, 2H, J=9Hz) |
| 106 | S | 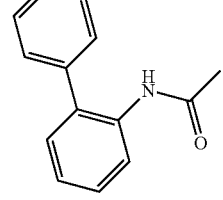 | (500 MHz, CD₃OD, HBr salt) 7.40 (m, 4H), 7.31 (m, 4H), 7.22 (m, 1H) |
| 107 | S | 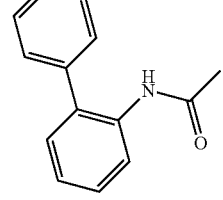 | (500 MHz, CD₃OD, HBr salt) 7.30 (m, 4H), 7.06 (t, 1H, J=7.5 Hz), 6.92 (m, 4H) |
| 108 | S | 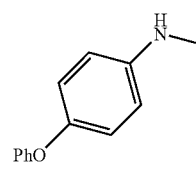 | (500 MHz, CD₃OD, HBr salt) 7.25 (m, 2H), 7.11 (t, 1H, J=8.2 Hz), 6.72 (m, 1H) |
| 109 | S | 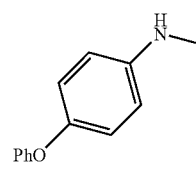 | (500 MHz, CD₃OD, HBr salt) 7.60 (d, 1H, 8 Hz), 7.06 (t, 1H, J=7 Hz), 6.87 (t, 1H, J=7Hz), 3.86 (s, 3H, OC$\underline{H}_3$) |
| 110 | S | 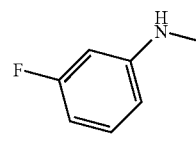 | (500 MHz, CD₃OD, HBr salt) 7.41 (d, 2H, J=8.2Hz), 7.18 (d, 2H, J=8.2 Hz) |
| 111 | S | 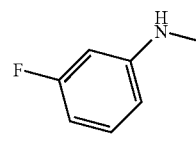 | (500 MHz, CD₃OD, HCl salt) 8.11 (d, 2H, J=8.1Hz), 7.68 (d, 2H, J=8.1 Hz), 4.36 (bs, 2H, C$\underline{H}_2$-Ph), 3.92 (s, 3H, OC$\underline{H}_3$) |

TABLE 6-continued

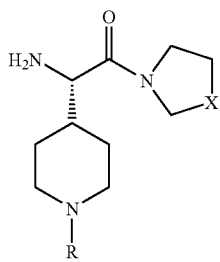

| Example | X | R | ¹H NMR data |
|---|---|---|---|
| 112 | S | ![4-tert-butylbenzyl] | (500 MHz, CD₃OD, HCl salt) 7.53 (d, 2H, J=8.2Hz), 7.47 (d, 2H, J=8.2Hz), 4.27 (s, 2H, C$\underline{H}_2$-Ph), 1.33 (s, 9H) |
| 113 | S | ![4-cyanobenzyl] | (500 MHz, CD₃OD, HCl salt) 7.85 (d, 2H, J=8.0 Hz), 7.78 (d, 2H, J=8.0 Hz), 4.41 (s, 2H, C$\underline{H}_2$-Ph) |
| 114 | S | ![4-trifluoromethylbenzyl] | (500 MHz, CD₃OD, HCl salt) 7.80 (s, 4H), 4.84 (s, 2H, C$\underline{H}_2$-Ph) |

EXAMPLE 115

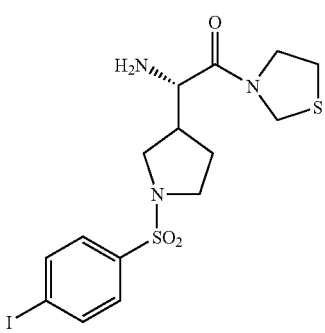

Step A. azido[1-(tert-butoxycarbonyl)pyrrolidin-3-yl]acetic acid

To a solution of 6.6 g (27.13 mmol) of tert-butyl 3-(2-methoxy-2-oxoethyl)pyrrolidine-1-carboxylate in methanol (150 mL) was added 25 mL (50 mmol) of 2N aqueous NaOH dropwise and the mixture was stirred at room temperature overnight. The solvent was removed under vacuum and the residue was acidified with 2N hydrochloric acid at 0° C. The organics were extracted with ethyl acetate (×3), washed with brine, dried over anhydrous Na₂SO₄, and filtered. Evaporation of the solvent gave 5.67 g of [1-(tert-butoxycarbonyl)-pyrrolidin-3-yl]acetic acid. The acid (5.64 g, 24.6 mmol) was converted to the title compound (4.2 g) in 3 steps using the procedure outlined in Example 6. ¹H NMR (500 MHz, CDCl₃) δ 3.64–3.53 (m, 3H), 3.32 (m, 1H), 3.20 (m, 1H), 2.59 (m, 1H), 2.21 (m, 1H), 1.81 (m 1H), 1.49 (s, 9H).

Step B. 3-[(2S)-2-Azido-2-pyrrolidin-3-ylethanoyl]-1,3-thiazolidine

Azido[1-(tert-butoxycarbonyl)pyrrolidin-3-yl]acetic acid (Example 97, step A, 810 mg, 2.9 mmol) was converted to the title compound (698 mg) in 2 steps using the procedure outlined in Example 94, step C. ¹H NMR (500 MHz, CD₃OD) δ 4.72–4.54 (m, 2H), 4.42 (d, 1/2H, J=7.1 Hz), 3.95 (d, 1/2H, J=7.1 Hz), 3.95–3.76 (m, 2H), 3.43 (m, 2H), 3.26 (m, 2H), 3.17–3.07 (m, 2H), 2.94 (m, 1H), 2.21 (m, 1H), 2.20 (m, 1H).

Step C. (1S)-1-{1-[(4-iodophenyl)sulfonyl]pyrrolidin-3-yl}-2-oxo-2-(1,3-thiazolidin-3-yl)ethanamine

To a solution of 28 mg (0.1 mmol) of 3-[(2S)-2-azido-2-pyrrolidin-3-ylethanoyl]-1,3-thiazolidine in methylene chloride (1 mL) was added 0.030 mL of diisopropylamine and 29 mg (0.12 mmol) of 4-iodobenzenesulfonyl chloride. The mixture was stirred for 18 h and subjected directly to preparative TLC on silica gel (eluent: 60% ethyl acetate in hexanes) to give the desired sulfonamide (40 mg) as an off white solid. This solid was dissolved in wet THF (10%) and 25 mg (0.1 mmol) of triphenyl phosphine was added and stirred at 60° C. for 5 h and concentrated. A mixture of diastereomers were separated by preparative TLC on silca gel (10% methanol in CH₂Cl₂). Diastereomer I (faster moving isomer) ¹H NMR (500 MHz, CDCl₃) δ 7.9 (d, 2H, J=8.1 Hz), 7.52 (d, 2H, J=8.1 Hz), 4.65–4.47 (m, 2H), 3.86 (m, 1H), 3.78 9 (dd, 1H, J=6 and 8 Hz), 3.43 (m, 1H), 3.25–3.02 (m, 4H), 2.4 (m, 1H), 1.95 (m, 2H). Diastereomer II (slower moving isomer) ¹H NMR (500 MHz, CDCl₃) δ 7.91 (d, 2H, J=8.2 Hz), 7.56 (d, 2H, J=8.2 Hz), 4.63–4.41 (m, 2H), 3.86 (m, 1H), 3.79 (m, 0.5H), 3.64 (m, 0.5H), 3.37 (m, 3H), 3.25 (dd, 1H, J=10 and 14 Hz), 3.12 (m, 2H), 3.01 (t, 1H, J=4.4 Hz), 2.4 (m, 1H), 1.94 (m, 1H), 1.61 (m, 1H).

Essentially following the procedures outlined for Example 115 the compounds listed in Table 7 were prepared.
TABLE 7
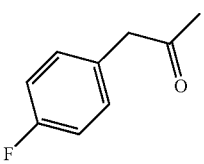
| Example | Isomer | X | R | ¹H NMR data |
|---------|--------|---|---|-------------|
| 116 | mix | S | 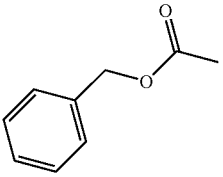 | (500 MHz, CDCl₃) 7.23 (m, 2H), 6.99 (m, 2H), 4.63 (m, 2H, C$\underline{H}_2$-Ph) |
| 117 | I | S | 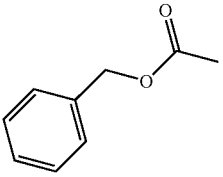 | (500 MHz, CDCl₃) 7.4–7.32 (m, 5H), 5.12 (d, 2H, J=12 and 17Hz, C$\underline{H}_2$-Ph) |
| 118 | II | S | 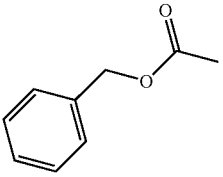 | (500 MHz, CDCl₃) 7.39–7.29 (m, 5H), 5.14 (s, 2H, C$\underline{H}_2$-Ph) |
| 119 | II | S | 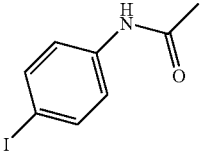 | (500 MHz, CDCl₃) 7.55 (d, 2H, J=8.6 Hz), 7.21 (d, 2H., J=8.6 Hz) |
| 120 | II | S | 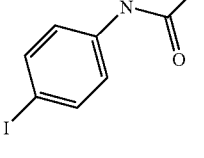 | (500 MHz, CDCl₃) 7.55 (d, 2H, J=8.2 Hz), 7.22 (d, 2H., J=8.2 Hz) |
| 121 | I | S | 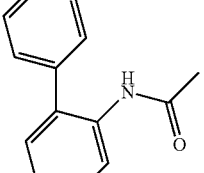 | (500 MHz, CDCl₃) 8.20 (m, 1H), 7.48 (m, 2H), 7.39 (m, 3H), 7.30 (m, 1H), 7.20 (m, 1H), 7.08 (m, 1H) |

TABLE 7-continued

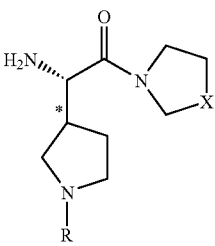

| Example | Isomer | X | R | $^1$H NMR data |
|---|---|---|---|---|
| 122 | II | S | 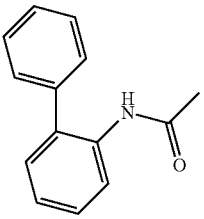 | (500 MHz, CDCl$_3$) 8.22 (d, 0.6H, J=8Hz), 8.18 (d, 0.4H, J=8Hz), 7.48 (m, 2H), 7.40 (m, 3H), 7.35 (m, 1H), 7.20 (m, 1H), 7.08 (m, 1H) |
| 123 | mix | S | 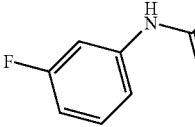 | (500 MHz, CDCl$_3$) 7.36 (m, 2H), 7.28 (m, 2H), 7.05 (t, 1H, J=7.2 Hz), 6.96 (m, 4H) |
| 124 | I | S | 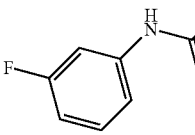 | (500 MHz, CDCl$_3$) 7.38 (d, 1H, J= 11 Hz), 7.22 (dd, 1H, J=8 and 11 Hz), 7.03 (d, 1H, J=8Hz), 6.72 (dd, J=7 and 11 Hz), 6.33 (bd, 1H, N$\underline{H}$) |
| 125 | II | S | 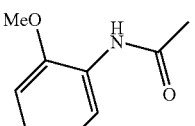 | (500 MHz, CDCl$_3$) 7.39 (d, 1H, J= 11 Hz), 7.22 (dd, 1H, J=8 and 11 Hz), 7.05 (d, 1H, J=8Hz), 6.71 (dd, J=7 and 11 Hz), 6.46 (bd, 1H, N$\underline{H}$) |
| 126 | mix | S | 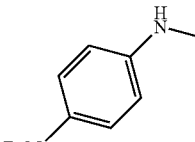 | (500 MHz, CD$_3$OD) 7.80 (m, 1H), 7.01 (m, 1H), 6.97 (m, 1H), 6.87 (m, 1H), 3.87 (s, 1.35H, OC$\underline{H}_3$), 3.86 (s, 1.65H, OC$\underline{H}_3$) |
| 127 | I | S | 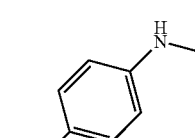 | (500 MHz, CDCl$_3$) 7.44 (d, 2H, J= 8.5Hz), 7.10 (d. 2H, , J=8.5Hz) |
| 128 | II | S |  | (500 MHz, CDCl$_3$) 7.43 (d, 2H, J= 8.4Hz), 7.07 (d. 2H, , J=8.4Hz) |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

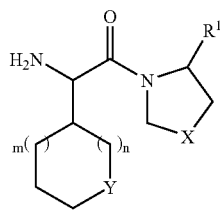

wherein:

X is selected from —S—, —S(O)—, —S(O)$_2$—, —CH$_2$—, —CHF—, and —CF$_2$—;

Y is selected from CH—(C$_{0-4}$alkyl-R$^2$) and N—R$^3$;

m is an integer selected from 0, 1 and 2, and n is an integer selected from 0, 1 and 2, with the proviso that the sum of m+n is 1 or 2;

R$^1$ is selected from hydrogen and —CN;

R$^2$ is selected from the group consisting of:
(1) —NR$^4$—CO—NR$^5$R$^6$,
(2) —NR$^4$—CO$_2$R$^6$,
(3) —NR$^4$—COR$^6$,
(4) —NR$^5$R$^6$,
(5) —NH$_2$,
(6) —NR$^4$—S(O)$_2$—R$^6$,
(7) —S(O)$_2$—NR$^5$R$^6$,
(8) —CO—NR$^5$R$^6$,
(9) —O—CO—NR$^5$R$^6$,
(10) —OH,
(11) —O—R$^6$,
(12) —R$^6$, and
(13) hydrogen, with the proviso that R$^2$ is hydrogen only if X is —CHF— or —CF$_2$—;

R$^3$ is selected from the group consisting of:
(1) —CO—NR$^5$R$^6$,
(2) —CO$_2$R$^6$,
(3) —COR$^6$,
(4) —S(O)$_2$—R$^6$,
(5) —R$^6$, and
(6) hydrogen, with the proviso that R$^3$ is hydrogen only if X is —CHF— or —CF$_2$—;

R$^4$ and R$^5$ are independently selected from hydrogen and C$_{1-6}$alkyl;

R$^6$ is independently selected from:
(1) C$_{1-10}$alkyl, which is unsubstituted or substituted, where the substituents are independently selected from:
(a) hydroxy,
(b) —O—C$_{1-6}$alkyl,
(c) halogen,
(d) phenyloxy, and
(e) —CN;

(2) phenyl, phenyloxy, C$_{1-6}$alkyl-phenyl, naphthyl, C$_{1-6}$alkyl-naphthyl, biphenyl, C$_{1-6}$alkyl-biphenyl, wherein the phenyl, naphthyl, or biphenyl, is unsubstituted or substituted, where the substituents are independently selected from:
(a) halogen,
(b) —OCF$_3$,
(c) —CF$_3$,
(d) —CHF$_2$,
(e) —CH$_2$F,
(f) C$_{1-10}$alkyl,
(g) —O—C$_{1-6}$alkyl,
(h) —O-phenyl, wherein the phenyl is unsubstituted or substituted, where the substituents are independently selected from:
(i) halogen,
(ii) —OCF$_3$,
(iii) —CF$_3$,
(iv) C$_{1-6}$alkyl, and
(v) —O—C$_{1-6}$alkyl,
(i) —CN,
(j) hydroxy,
(k) —NR$^8$R$^9$, wherein R$^8$ and R$^9$ are independently selected from hydrogen and C$_{1-6}$alkyl, or R$^8$ and R$^9$ are joined together with the nitrogen to form a 5–6 membered ring,
(l) —NR$^4$—CO—NR$^8$R$^9$,
(m) —NR$^4$—S(O)$_2$—C$_{1-6}$alkyl,
(n) —CO—NR$^8$R$^9$,
(o) —CO$_2$—C$_{1-6}$alkyl,
(p) —O—CO—NR$^8$R$^9$, and
(q) heterocycle, wherein the heterocycle is unsubstituted or substituted, where the substituents are independently selected from:
(i) halogen,
(ii) oxo,
(iii) C$_{1-10}$alkyl-(C$_{3-6}$cycloalkyl),
(iv) C$_{1-10}$alkyl, which is unsubstituted or substituted with up to 5 halogen,
(v) —O—C$_{1-6}$alkyl, which is unsubstituted or substituted with up to 5 halogen,
(vi) C$_{0-6}$alkyl-phenyl, wherein the phenyl is unsubstituted or substituted, where the substituents are independently selected from:
(I) halogen,
(II) —OCF$_3$,
(III) —CF$_3$,
(IV) C$_{1-6}$alkyl, and
(V) —O—C$_{1-6}$alkyl,
(vii) pyridyl, and
(viii) —CO—C$_{1-6}$alkyl; and (3) heterocycle, and C$_{1-6}$alkyl-heterocycle, wherein the heterocycle is unsubstituted or substituted, where the substituents are independently selected from:
(a) halogen,
(b) oxo,
(c) C$_{1-10}$alkyl-(C$_{3-6}$cycloalkyl),
(d) C$_{1-10}$alkyl, which is unsubstituted or substituted with up to 5 halogen,
(e) —O—C$_{1-6}$alkyl, which is unsubstituted or substituted with up to 5 halogen,
(f) C$_{0-6}$alkyl-phenyl, wherein the phenyl is unsubstituted or substituted, where the substituents are independently selected from:
(i) halogen,
(ii) —OCF$_3$,
(iii) —CF$_3$, (iv) C$_{1-6}$alkyl, and
(v) —O—C$_{1-6}$alkyl,
(g) pyridyl, and
(h) —CO—C$_{1-6}$alkyl;
and pharmaceutically acceptable salts thereof and individual diastereomers thereof.

2. The compound of claim 1 of the formula Ia:

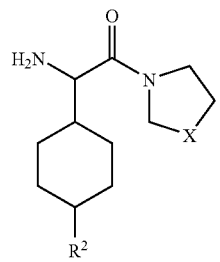

Ia wherein:
X and R$^2$ are defined in claim 1;
and pharmaceutically acceptable salts and individual diastereomers thereof.

3. The compound of claim 1 of the formula Ib:

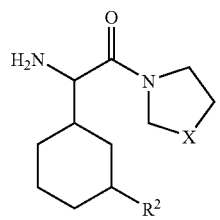

Ib wherein:
X and R$^2$ are defined in claim 1;
and pharmaceutically acceptable salts and individual diastereomers thereof.

4. The compound of claim 1 of the formula Ic:

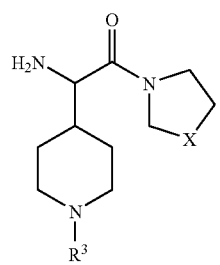

Ic wherein X and R$^3$ are defined in claim 1;
and pharmaceutically acceptable salts thereof and individual diastereomers thereof.

5. The compound of claim 1 of the formula Id:

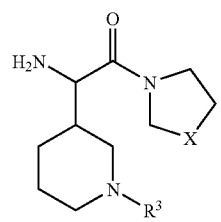

Id wherein X and R$^3$ are defined herein;
and pharmaceutically acceptable salts thereof and individual diastereomers thereof.

6. The compound of claim 1 of the formula Ie:

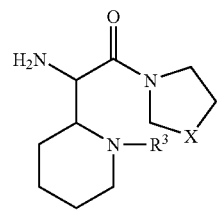

Ie wherein X and R$^3$ are defined herein;
and pharmaceutically acceptable salts thereof and individual diastereomers thereof.

7. The compound of claim 1 of the formula If:

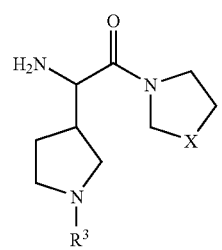

If wherein X and R$^3$ are defined herein;
and pharmaceutically acceptable salts and individual diastereomers thereof.

8. The compound of claim 1 wherein X is selected from —S—, —CH$_2$—, —CHF— and —CF$_2$—.

9. The compound of claim 1 wherein R$^1$ is hydrogen.

10. The compound of claim 1 wherein R$^2$ is selected from the group consisting of:
(1) —NR$^4$—CO—NR$^5$R$^6$,
(2) —NR$^4$—CO$_2$R$^6$,
(3) —NR$^4$—COR$^6$, and
(4) —NR$^4$—S(O)$_2$—R$^6$.

11. The compound of claim 1 wherein R$^3$ is selected from the group consisting of:
(1) —CO—NR$^5$R$^6$,
(2) —CO$_2$R$^6$,
(3) —COR$^6$, and
(4) —S(O)$_2$—R$^6$.

12. The compound of claim 1 wherein R$^4$ and R$^5$ are independently selected from hydrogen and methyl.

13. The compound of claim 1 wherein $R^6$ is independently selected from:
(1) phenyl and $C_{1-3}$alkyl-phenyl, wherein the phenyl is unsubstituted or substituted, where the substituents are independently selected from:
    (a) halogen,
    (b) —$OCF_3$,
    (c) —$CF_3$,
    (d) $C_{1-6}$alkyl,
    (e) —O—$C_{1-6}$alkyl, and
    (f) phenyloxy,
(2) naphthyl, wherein the naphthyl is unsubstituted or substituted, where the substituents are independently selected from:
    (a) halogen,
    (b) —$OCF_3$,
    (c) —$CF_3$,
    (d) $C_{1-6}$alkyl, and
    (e) —O—$C_{1-6}$alkyl,
(3) biphenyl, wherein the biphenyl is unsubstituted or substituted, where the substituents are independently selected from:
    (a) halogen,
    (b) —$OCF_3$,
    (c) —$CF_3$,
    (d) $C_{1-6}$alkyl, and
    (e) —O—$C_{1-6}$alkyl.

14. The compound of claim 1 of the formula

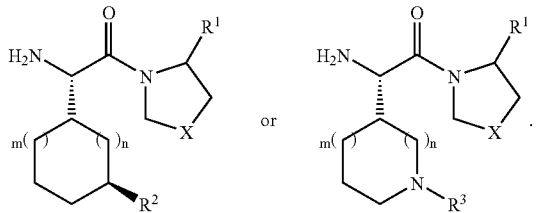

15. A pharmaceutical composition which comprises an inert carrier and a compound of claim 1.

16. A method for treating diabetes comprising the administration to a patient of an effective amount of the compound of claim 1.

17. A method for treating non-insulin dependent (Type 2) diabetes mellitus in a mammalian patient in need of such treatment which comprises administering to the patient a therapeutically effective amount of a compound of claim 1.

18. A method for treating hyperglycemia in a mammalian patient in need of such treatment which comprises administering to the patient a therapeutically effective amount of a compound of claim 1.

19. A method for treating insulin resistance in a mammalian patient in need of such treatment which comprises administering to the patient a therapeutically effective amount of a compound of claim 1.

20. A method for the treatment of one or more conditions selected from the group consisting of hypercholesterolemia, atherosclerosis, low HDL levels, high LDL levels, hyperlipidemia, hypertriglyceridemia, and dyslipidemia, which method comprises administering to a mammalian patient in need of such treatment a therapeutically effective amount of a compound of claim 1 and an HMG-CoA reductase inhibitor.

21. The method of claim 20, wherein the HMG-CoA reductase inhibitor is a statin.

22. The method of claim 21, wherein the statin is selected from the group consisting of lovastatin, simvastatin, pravastatin, fluvastatin, atorvastatin, itavastatin, ZD-4522 and rivastatin.

23. A pharmaceutical composition comprising
(1) a compound of claim 1,
(2) one or more compounds selected from the group consisting of:
    (a) insulin sensitizers selected from the group consisting of (i) PPARγ agonists, other PPAR ligands, PPARα/γ dual agonists, and PPARα agonists, (ii) biguanides, (iii) protein tyrosine phosphatase-1B (PTP-1B) inhibitors, and (iv) other dipeptidyl peptidase IV (DP-IV) inhibitors;
    (b) insulin or insulin mimetics;
    (c) sulfonylureas;
    (d) α-glucosidase inhibitors;
    (e) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γ dual agonists, (vi) inhibitors of cholesterol absorption, (vii) acyl CoA: cholesterol acyltransferase inhibitors, and (viii) anti-oxidants;
    (f) PPARδ agonists;
    (g) antiobesity compounds;
    (h) an ileal bile acid transporter inhibitor; and
    (i) anti-inflammatory agents; and
(3) a pharmaceutically acceptable carrier.

* * * * *